United States Patent
Bullington et al.

(10) Patent No.: US 10,854,330 B1
(45) Date of Patent: Dec. 1, 2020

(54) APPOINTMENT SCHEDULING MANAGEMENT SYSTEM

(71) Applicants: Deborah T Bullington, Jackson, WY (US); Andrew B Bullington, Jackson, WY (US)

(72) Inventors: Deborah T Bullington, Jackson, WY (US); Andrew B Bullington, Jackson, WY (US)

(*) Notice: Subject to any disclaimer, the term of this patent is extended or adjusted under 35 U.S.C. 154(b) by 1074 days.

(21) Appl. No.: 15/333,087

(22) Filed: Oct. 24, 2016

Related U.S. Application Data

(63) Continuation-in-part of application No. 14/794,857, filed on Jul. 9, 2015.

(51) Int. Cl.
| | |
|---|---|
| *G06Q 50/20* | (2012.01) |
| *G16H 40/20* | (2018.01) |
| *G06F 16/2457* | (2019.01) |
| *G06F 16/2458* | (2019.01) |

(52) U.S. Cl.
CPC ......... *G16H 40/20* (2018.01); *G06F 16/2457* (2019.01); *G06F 16/2477* (2019.01)

(58) Field of Classification Search
None
See application file for complete search history.

(56) References Cited

U.S. PATENT DOCUMENTS

| | | | | |
|---|---|---|---|---|
| 9,003,328 B1* | 4/2015 | Boutcher | ............... | G06Q 10/10 715/810 |
| 2005/0234741 A1* | 10/2005 | Rana | ................... | G06Q 10/107 705/2 |
| 2006/0184943 A1* | 8/2006 | DelMonego | ........... | G06Q 10/06 718/100 |
| 2006/0288095 A1 | 12/2006 | Torok et al. | | |
| 2007/0282654 A1* | 12/2007 | Sarkar | .............. | G06Q 10/06311 705/7.16 |
| 2009/0048865 A1* | 2/2009 | Breazeale, Jr. | ........ | G06Q 50/22 705/2 |
| 2009/0281825 A1 | 11/2009 | Larsen | | |
| 2010/0042441 A1* | 2/2010 | Steusloff | ................. | G06F 3/002 705/3 |

(Continued)

OTHER PUBLICATIONS

"U.S. Appl. No. 14/794,857, Non Final Office Action dated Dec. 11, 2018", 17 pgs.

(Continued)

*Primary Examiner* — Jonathan Ng
(74) *Attorney, Agent, or Firm* — Kwan & Olynick LLP

(57) ABSTRACT

Provided are mechanisms and processes for a medical appointment delay management system. According to various examples, the system includes a location sensor that detects when a medical professional wearing a personal beacon enters an examination room to conduct an examination of a particular patient. The system also includes a medical schedule processor that logs a time associated with when the medical professional enters the examination room and compares this time with scheduling information to predict whether future appointments in the schedule will be delayed. A notification interface, included in the system, is designed to notify an upcoming patient if their scheduled appointment will be substantially delayed. Scheduling information is cryptographically separated from HIPAA information.

20 Claims, 15 Drawing Sheets

(56) References Cited

U.S. PATENT DOCUMENTS

| | | | |
|---|---|---|---|
| 2010/0123560 A1* | 5/2010 | Nix | H04Q 9/00 |
| | | | 340/10.4 |
| 2013/0304534 A1* | 11/2013 | Mehta | G06Q 10/1095 |
| | | | 705/7.19 |
| 2014/0278679 A1* | 9/2014 | Navani | G06Q 10/06311 |
| | | | 705/7.19 |
| 2015/0213414 A1* | 7/2015 | Zuckerman | G06Q 10/1095 |
| | | | 705/7.19 |
| 2018/0150603 A1 | 5/2018 | Bullington et al. | |

OTHER PUBLICATIONS

U.S. Appl. No. 14/794,852, Non-Final Rejection, dated Feb. 21, 2020, 26 pgs.

U.S. Appl. No. 14/794,852, Examiner Interview Summary Record (Ptol-413), dated May 22, 2020, 2 pgs.

U.S. Appl. No. 14/794,854, Non-Final Rejection, dated Jan. 15, 2020, 5 pgs.

U.S. Appl. No. 14/794,854, Notice of Allowance and Fees Due (Ptol-85), dated Jun. 8, 2020, 7 pgs.

U.S. Appl. No. 14/794,857, Non-Final Rejection, dated Feb. 5, 2020, 15 pgs.

U.S. Appl. No. 16/151,148, Non-Final Rejection, dated Feb. 6, 2020, 5 pgs.

U.S. Appl. No. 16/151,148, Notice of Allowance and Fees Due (Ptol-85), dated May 29, 2020, 5 pgs.

* cited by examiner

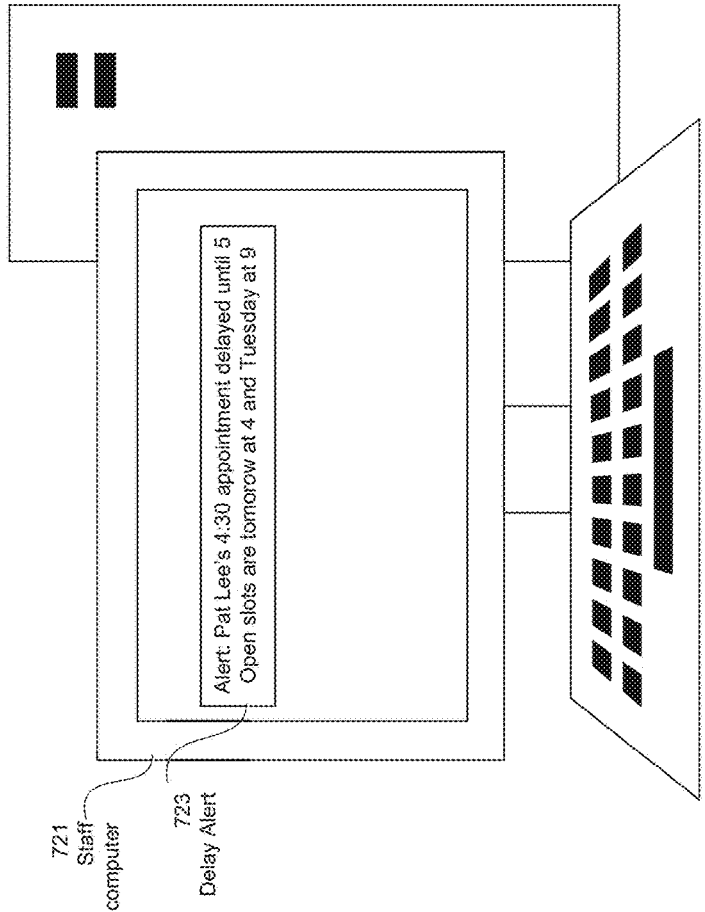
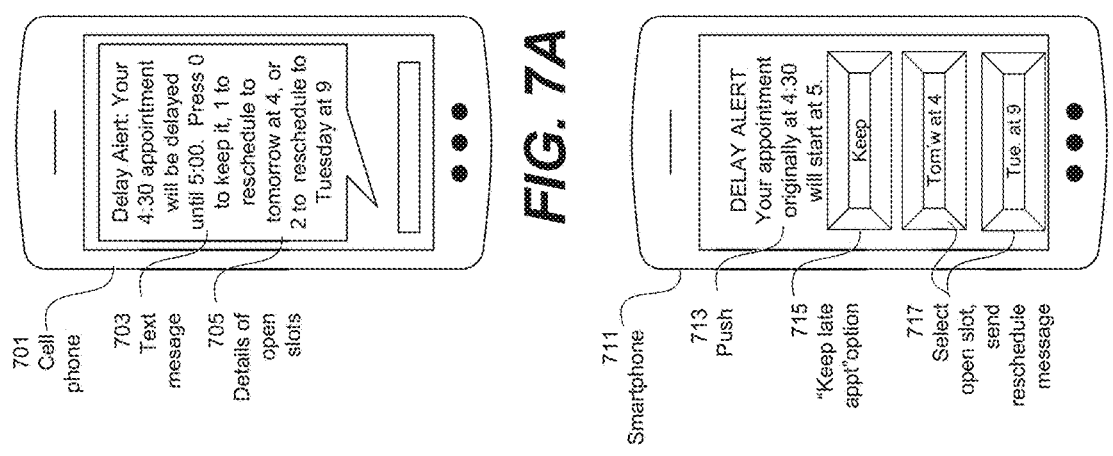
FIG. 7C
FIG. 7A
FIG. 7B

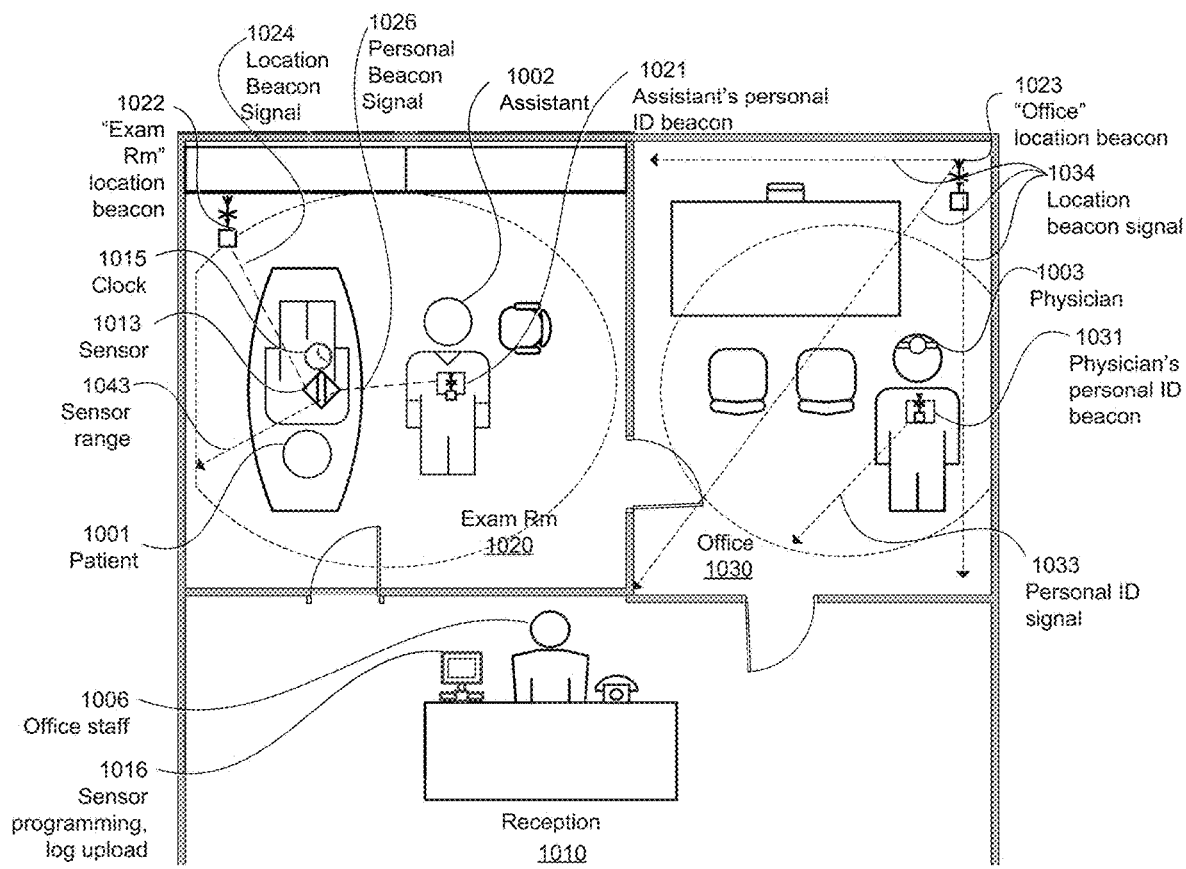
FIG. 10A
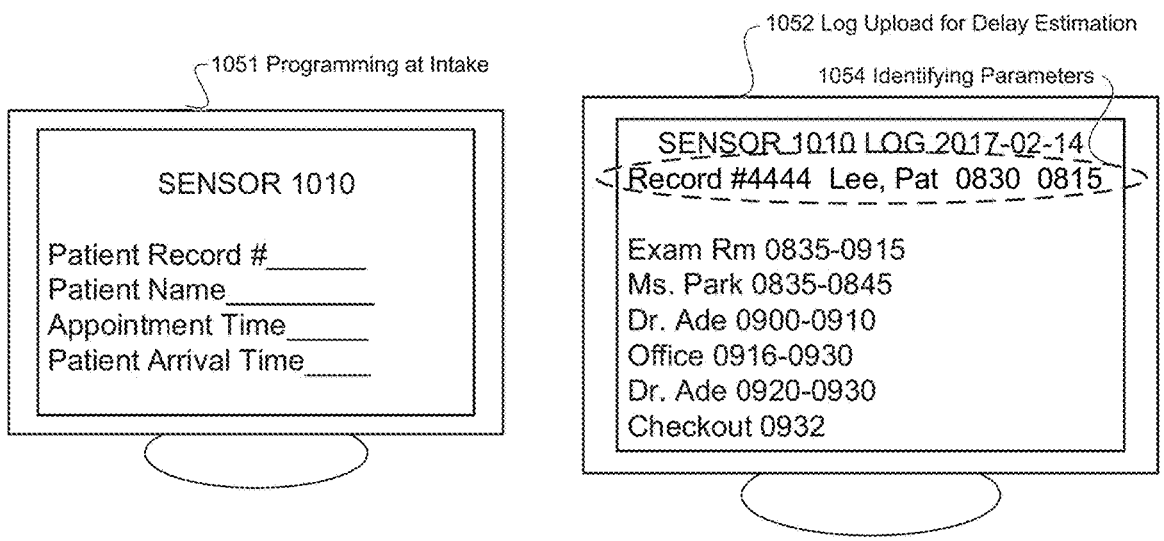
FIG. 10B  FIG. 10C

APPOINTMENT SCHEDULING MANAGEMENT SYSTEM

CROSS-REFERENCE TO RELATED APPLICATIONS

This application is a continuation-in-part of U.S. patent application Ser. No. 14/794,857 filed Jul. 9, 2015, which is entirely incorporated by reference herein.

BACKGROUND

Medical appointments are commonly associated with notoriously long wait times. According to numerous reviews from patients, the number one complaint is the wait time to see the doctor. For instance, online review sites allow patients to comment and provide corresponding star ratings for service providers. On these sites, low star ratings for physicians are often associated with comments citing long wait times. Often, reviewers complain of waiting from between thirty minutes to two hours. These reviews indicate that patient satisfaction with a physician's care can be heavily influenced by wait times, and that excessive wait times can lead to negative reviews of a physician's services.

Accordingly, improving the wait time for a patient can greatly improve the patient's satisfaction with the physician. In turn, this satisfaction will improve the patient's subjective feelings about their care, which can lead to more effective treatment and service. Specifically, when the patient is in a positive frame of mind at the beginning of the examination, the appointment naturally flows more smoothly. In addition, physicians often note that when they are behind schedule, they often spend time apologizing to the patient about being late, which reduces the amount of time available for actual patient care. By reducing or eliminating patient wait times, physicians can be more efficient and patients can have more positive experiences at appointments. Consequently, there is a need for improving patient wait times for medical appointments.

SUMMARY

Provided are various mechanisms and processes relating to an appointment scheduling management system. Although medical scheduling is used as a main example, those of ordinary skill in the art will recognize that the same problems may exist in any appointment-based service practice (including but not limited to dental, veterinary, legal, accounting, counseling, cosmetology, photography or auto repair concerns) and may accordingly be addressed by the subject matter of this disclosure.

In one aspect, which may include at least a portion of the subject matter of any of the preceding and/or following examples and aspects, provided systems may include a first beacon transmitting a first signal; a clock providing a local time, a memory storing at least a first scheduled time, a second scheduled time, and a delay threshold; a first sensor reactive to the first signal and to a position or motion of the first beacon; a processor coupled to the first sensor, the clock, and the memory; an appointment database coupled to at least one of the memory or the processor and comprising patient contact information and a date and time of at least one open appointment slot; a delay log coupled to the memory and accessible through an office interface; and a computing device programmed to display the office interface.

The first scheduled time and the second scheduled time may be different times at which the first sensor is expected to detect the first signal. The processor may include logic capable of subtracting the first scheduled time from the local time to compute a first delay, sending the first delay to the delay log, comparing the first delay to the delay threshold, and overwriting the second scheduled time if the first delay is greater than the delay threshold;

In some embodiments, a system may include a patient notification interface coupled to the memory, the appointment database, and at least one patient device. The patient device may include a telephone and the patient notification interface may alert a patient to the first delay by a text message or a voicemail. Alternatively, the patient device may include a computing device and the patient notification interface may alert a patient to the first delay by an email or a push notification.

In some embodiments, the patient notification interface may send details of the open appointment slot to the patient device. The patient notification interface may accept a rescheduling message from the patient device and responsively update at least one of the second scheduled time or the appointment database. The patient notification interface may cause the patient device to display options of keeping or rescheduling a delayed appointment.

In some embodiments, the first sensor may be coupled to activate an alert in response to the first beacon passing through a doorway. The first sensor may remain in or with an examination room or treatment room. The first beacon may be carried or worn by a first medical worker or first patient, and the processor may capture the local time and compute the first delay in response to the first sensor detecting an entry or an exit of the first beacon into or out from the examination room or treatment room. Alternatively, the first sensor may be carried or worn by the first medical worker or first patient while the first beacon remains in or with the examination room or treatment room.

In some embodiments, the system may also include a second sensor carried or worm by a second medical worker or second patient The processor may capture the local time and compute the first delay in response to a change in the first signal as detected by the first sensor or the second sensor.

According to various examples, provided non-transitory machine-readable information storage media may include code that, when executed, causes a machine to detect a position or a motion of a first beacon relative to an examination or treatment room and log a local time when the first beacon enters or exits the examination or treatment room during a first appointment. The code may additionally cause the machine to retrieve a first scheduled time associated with the entry or exit, subtract the first scheduled time from the local time to estimate a first delay, and compare the first delay to a first threshold.

If the first delay is greater than the first threshold, the code may cause the machine to retrieve a second scheduled time associated with a second appointment, add the first delay to the second scheduled time to compute a revised time associated with the second appointment, and notify a communication device that the second appointment will be delayed until the revised time.

In some embodiments, the code may cause the communication device to display a selectable "keep" option and a selectable list of open appointment slots. If a user selects the "keep" option, the code may cause the system to replace the second scheduled time with the revised time. If the user selects a substitute appointment from the list of open appointment slots, the code may cause the system to cancel the second appointment and assign the substitute appointment to a patient formerly holding the second appointment, In some embodiments, the communication device may include a mobile device. The communication device may include a remote device used by the patient or a computing device used by office staff.

In some embodiments, the code may cause the machine to determine whether the detected entry or exit is a gating event (i.e., an event that definitively indicates an expected delay of the next appointment). If the detected entry or exit is not a gating event, the code may cause the machine to return to detection rather than use the non-gating event to calculate a possibly inaccurate delay. In some embodiments, the delays are only computed from the local times of gating events. Optionally, the gating event may be identified after a subsequent confirming event is detected; e.g., detecting an entry of Patient B into the exam room (confirming event) confirms that the last detected exit of previous Patient A from the exam room was the end of Patient A's appointment (gating event).

In some embodiments, the code may include instructions for programming the first beacon to transmit an identity signal associated with a wearer, so that each wearer's beacon transmits a different distinguishable signal. The code may then cause the machine to log a corresponding wearer identity along with the local time upon detecting an entry or exit. Optionally, delay log entries may be stored in a database. The database may be analyzed to identify frequent causes, lengths, or types of appointment delays so that bottlenecks and the like can be mitigated and the office can potentially improve its on-time performance.

Embodiments of the system and software may be scaled for virtually any size of practice, and may include contingencies for variations in the practice's routine.

BRIEF DESCRIPTION OF THE DRAWINGS

FIGS. 7A-7C illustrate examples of user interface screens for the appointment management system.

FIGS. 10A-10C are diagrams illustrating one example of a system in which sensors are worn by patients and identifier beacons are worn by employees and placed in service locations.

DETAILED DESCRIPTION OF EXAMPLE EMBODIMENTS

Figure 1:
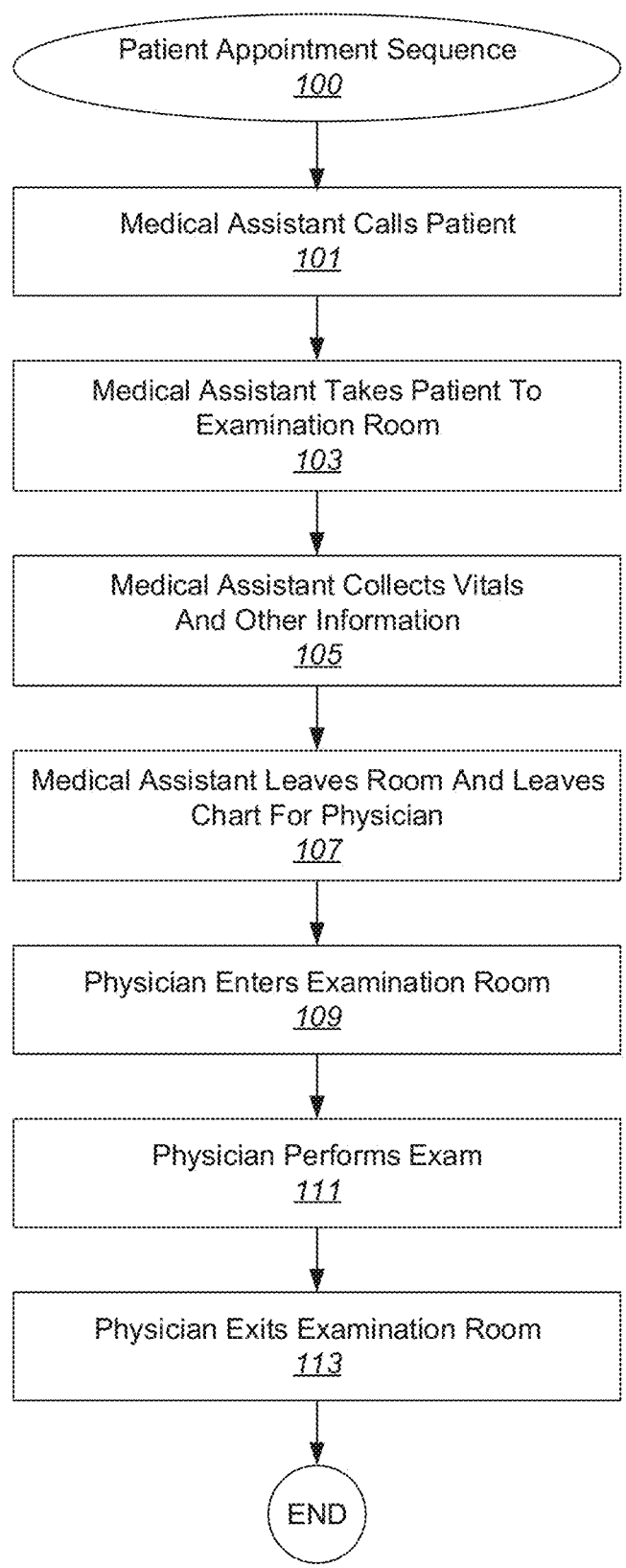
FIG. 1 is a flow chart illustrating one example of a patient appointment sequence.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques of the present invention will be described in the context of particular scheduling mechanisms for medical offices. However, it should be noted that the techniques of the present invention apply to a wide variety of different scheduling mechanisms for a variety of different types of service entities such as dental offices, vision service providers, etc. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Medical appointments are commonly associated with notoriously long wait times. Because patient satisfaction with a physician's care can be heavily influenced by wait times, excessive wait times can lead to negative reviews of a physician's services. By reducing or eliminating patient wait times, physicians can be more efficient and patients can have more positive experiences at medical offices. The same applies to other providers of services by appointment whose schedules may be subject to delays for various reasons.

Accordingly, various embodiments of the present invention address the issue of wait times in medical offices. In some examples, a physician's progress is monitored and any delays in the physician's schedule are detected. Patients are then informed of any delays or schedule changes in real-time. Specifically, a medical scheduling management system tracks the physician's progress and provides notifications, such as through text messages, to upcoming patients. These notifications can let patients know when a physician is running behind and ask them to arrive later than their originally scheduled appointment.

By notifying patients in real-time about schedule changes or fluctuations, the intent is to decrease the amount of time that each patient waits for their appointment to begin. In turn, reducing the wait time should increase patient satisfaction and result in more positive experiences with their physicians.

Because reimbursement according to programs like Medicare will be highly dependent on patient satisfaction in the future, the amount physicians will be paid will be closely tied to their patients' satisfaction. By keeping patients informed of schedule status and changes, the system described in various examples of this disclosure has the potential to address one of the biggest problems with patient satisfaction: wait times. If patient satisfaction is increased, then there is a higher likelihood that physicians will be fully reimbursed for their work. In addition, higher patient satisfaction will also lead to more referrals from patients and more business for physicians.

According to various embodiments, physician and other service employee activities, movements, and locations can be automatically or manually detected to allow improved appointment scheduling. For example, appointment start times can be manually or automatically triggered when a physician enters or a room and characteristics of the appointment can be used to determine whether later appointments need to be adjusted.

In particular embodiments, mechanisms for tracking physician or other medical personnel activities, movements, and locations for scheduling appointments are firewalled from systems managing patient medical data. In some examples, different encryption mechanisms are used to encode patient medical data and medical personnel scheduling data so that access to one system does not permit access to another system. In other examples, different networks such as different virtual networks or different physical networks are used to transport the different types of data. According to various embodiments, patient medical data is encrypted during both storage and transmission using a different mechanism from medical personnel tracking data.

With reference to FIG. 1, shown is a flow chart illustrating one example of a patient appointment sequence. As shown, a typical patient appointment sequence 100 begins when a medical assistant (or nurse in some cases), calls a patient at 101 from the waiting room. Various embodiments will be described with reference to particular medical personnel. However, it should be noted that numerous activities can be performed by a variety of different medical professionals such as medical staff, medical assistants, nurses, physician assistants, physicians, residents, etc. A variety of triggers can also be used to initiate scheduling mechanisms, such as when a physician enters the patient's examination room, when a physician leaves the patient's examination room, when a nurse brings a patient to an examination room, etc.

According to various embodiments, a medical assistant then takes the patient to the examination room at 103. During the medical assistant's session with the patient, the medical assistant often collects information such as vitals and other data at 105. This may include aspects such as measuring temperature, blood pressure, and the like. In addition, this process can include weighing and measuring the height of the patient. In some cases, these measurements may be taken in a hallway on the way to the examination room. The medical assistant may also ask the patient questions and take notes. The medical assistant then leaves the examination room and leaves the patient's chart for the physician at 107. The patient is then left alone in the examination room to wait for the physician. This time may also be used for changing into a gown, etc.

Next, the physician enters the examination room at 109. The physician performs the exam at 111, and then exits the examination room at 113. This concludes the process and the patient changes clothes, if appropriate, and collects their belongings before leaving the examination room.

As described, a medical appointment includes various phases that may include wait times. For instance, the patient may wait for a period of time before the medical assistant initially calls the patient at 101. The patient may also wait for a period of time between the time the medical assistant leaves the room at 107 and the time the physician enters the room at 109. Both of these wait times affect patient satisfaction and can lead to complaints relating to patient care. In addition, the amount of time that a physician spends with a particular patient, between blocks 109 and 113, affects whether future appointments that day will be on time or delayed. Accordingly, the timing of various phases of a patient appointment sequence can affect patient satisfaction and determine whether future appointments will be delayed.

FIGS. 2A-2E are diagrams illustrating one example of a system of sensors, identifiers, and their signals.

Figure 2A:
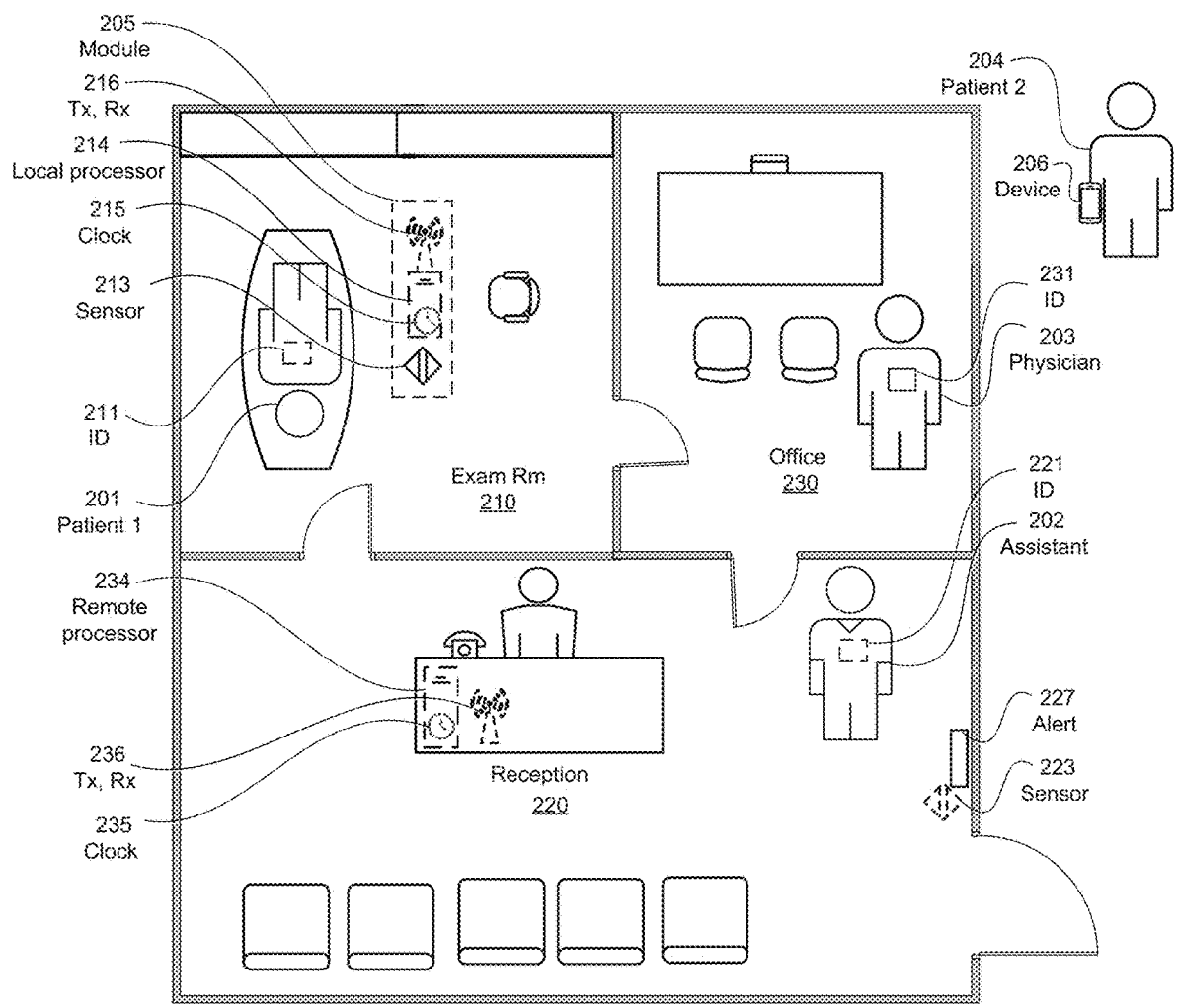
FIGS. 2A-2E are diagrams illustrating one example of a system of sensors, identifiers, and their signals.

With reference to FIG. 2A, shown is an example of a partial medical-office floor plan with an example of the system installed. Physician 203, shown in office 230, is the wearer of physician's identifier 231. Physician's identifier (ID) 231 may be an active beacon or a non-powered readable tag such as an RFID or infrared tag. In this example, office 230 does not have any sensors; for example, it may be used for purposes that do not involve the presence of patients.

In some embodiments, only the physician might wear an ID if his or her availability primarily affects a patient's waiting time. If more than one person wears an identifier, each of the identifiers may optionally expose or transmit a unique parameter. The parameter may include the wearer's role ("Doctor"), name ("Dr. Smith"), or any other encodable information linking the detected ID with its wearer. Such identification parameters allow the sensor to record who is entering or exiting a service location as well as when they enter or exit.

In some embodiments, assistant 202 also wears an ID, distinguishable by the sensor(s) as assistant's identifier 221. As illustrated, assistant's identifier 221 may be in position to be detected by door sensor 223 in waiting room 220. Door sensor 223 may activate door alert 227 to keep patients from inadvertently leaving with their IDs. Alternatively, door sensor 223 may simply record entry and exit of ID-wearers through the main office door. Door sensor 223 is logged by remote processor 234, which has a dedicated clock 235 and transmitter/receiver 236. In some embodiments, remote processor 234 is a hub processor for multiple sensors.

Patient 201, who has the current appointment, waits in service location 210, an exam room. Optionally, patient 201 may wear a patient's identifier 211. Patient ID 211 may help locate the patient in the office if there is any confusion about where he or she is. Logging patient ID 211's interactions with door sensor 223 may also isolate the variable of patient arrival time if the sensor data on appointment timing is to be analyzed.

Also in exam room 210 is an exam-room sensor 213. As illustrated, exam-room sensor 213 is part of a self-contained sensor module 205, another optional configuration for location sensors. Also in sensor module 205 are dedicated sensor processor 214, dedicated clock 215, and sensor transmitter/receiver 216.

Delays and other events logged by sensors may trigger alerts on office employees' devices (mobile or not). For practices that emphasize human contact, that notification may be sufficient; an employee would then personally contact a patient with a delayed upcoming appointment and explain options. By contrast, in a practice that prefers to reach patients via technology may use an embodiment that sends scheduling updates to device 206 accessed by upcoming patient 204, a holder of a later appointment.

Figure 2B:
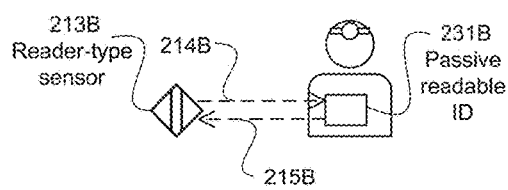

With reference to FIG. 2B, shown is a diagram of detection of a passive readable ID. ID 231B does not have its own power source. Sensor 213B emits signal 214B, which impinges on ID 231B and is returned as return signal 215B/. For example, ID 231B may be an RFID tag that, when within range of sensor 213B, takes power 214B from sensor 213B and uses it to emit its own signal 215B for detection by sensor 213B. As another example, ID 231B may be a bar or QR code and sensor 213B may include a scanning laser. The laser beam 214B (e.g., an eye-safe low-power infrared laser) is reflected or scattered from a coded pattern (e.g., a barcode or QR code) on ID 231B. The reflected or scattered light goes back to sensor 213B as return signal 215B.

Figure 2C:
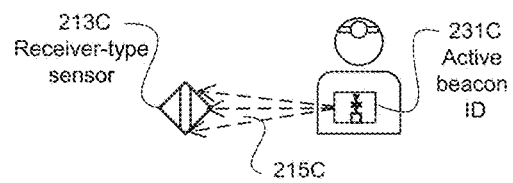

With reference to FIG. 2C, shown is a diagram of detection of an emitted signal from an active beacon ID. ID 231C had its own power source enabling it to independently emit signal 215C toward sensor 213C. For example, beacons available at the time of this writing have dimensions on the order of 5-10 cm (2-4"), weights of less than 1 ounce, and line-of-sight ranges of a few centimeters to a few hundred meters, depending partially on whether their signals are Bluetooth™, Bluetooth Low Energy (BTLE)™, ANT+™, IEEE 802.22™ IrDA™, NFC™ RFID™ Wi-Fi™, ZigBee™, wireless USB or HART, or some other signal type. Some active beacons have built-in sensors for motion, light, magnetic fields, heat, and other quantities. A beacon with a built-in sensor could potentially function as either a beacon or a sensor, so that only one type of unit needs to be ordered, deployed, and tracked. Some active beacons with built-in processors and memory may be reprogrammed to change their signal characteristics, either to uniquely identify particular beacons or to avoid interference with medical equipment. Such beacons may, for example, be shared by employees whose shifts do not overlap or patients whose appointments do not overlap. In either case, beacon 231C may be reprogrammed between uses to transmit the identifying parameter of the next wearer rather than the preceding one.

Figure 2D:
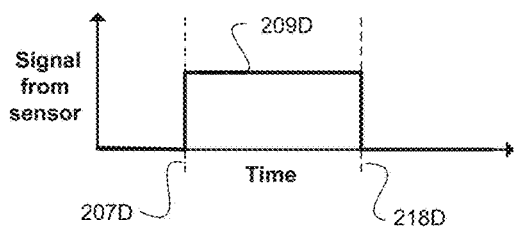

With reference to FIG. 2D, shown is one type of sensor signal from which entry and exit times may be derived. The sensor emits a signal 209D as long as it detects an ID in range, and emits no signal (at least, no signal associated with that particular ID) while the ID is out of range. This the processor will read upward transition 207D as an entry and downward transition 218D as an exit.

Figure 2E:
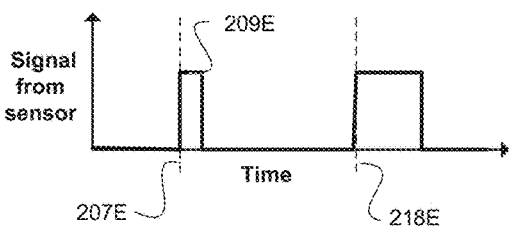

With reference to FIG. 2E, shown is another type of sensor signal from which entry and exit times may be derived. The sensor sends a first pulse 209E at time 207E when an ID comes within the sensor's range, emits no signal associated with that particular sensor while it remains inn range, then emits a second pulse at time 218E in response to the ID moving out of the sensor range.

In some embodiments, it may be preferable to conserve beacon power; this schema uses significantly less power than emitting a signal continuously as in FIG. 2D. Distinguishing between entry and exit may be done via pulse length, as here, but alternatively by frequency, number of pulses, attack/release waveform, or the like.

Figure 3:
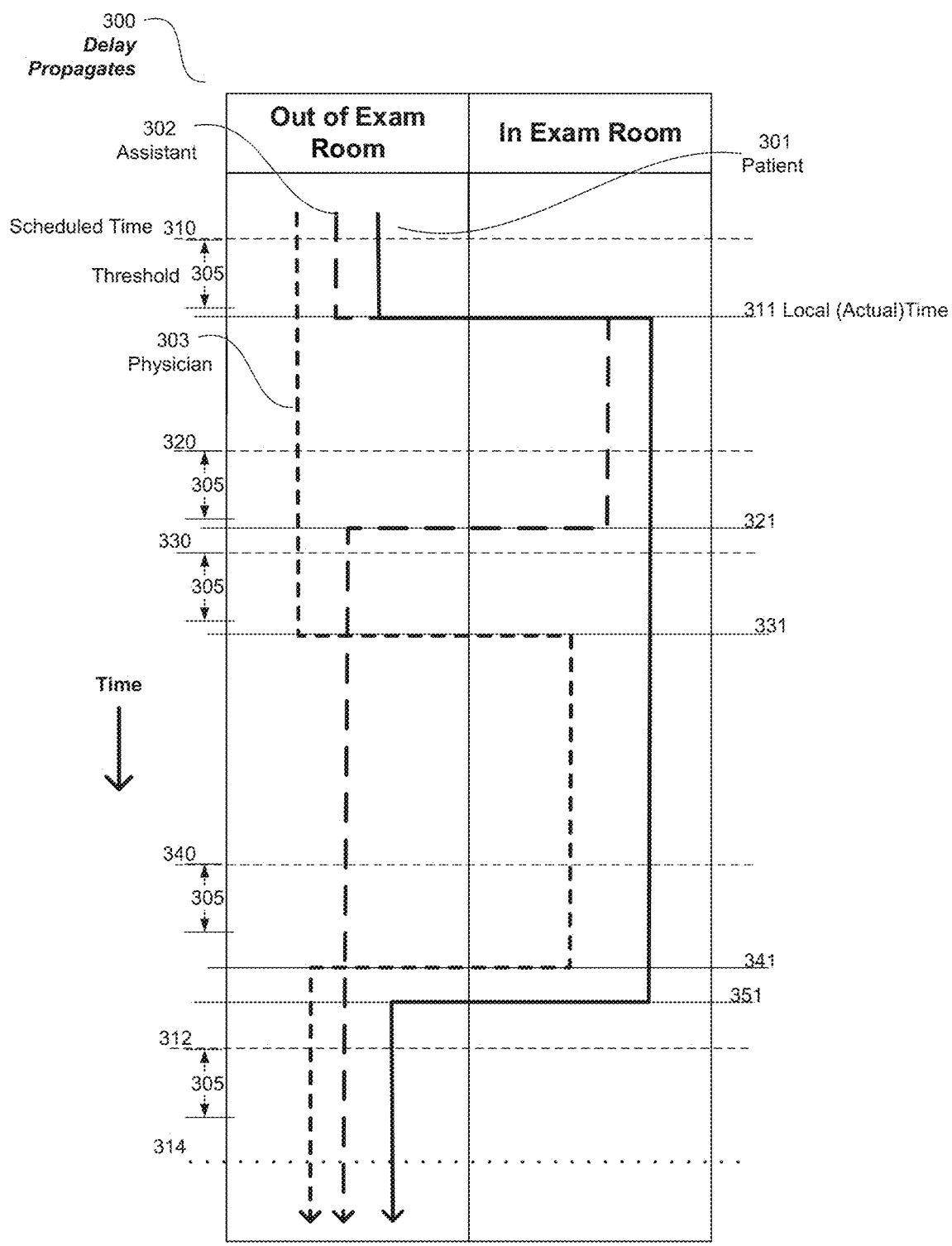
FIG. 3 is a swim-lane diagram of propagating delays of appointments.

With reference to FIG. 3, shown is a swim-lane diagram of propagating delays in appointments. This figure graphically represents the appointment routine described with reference to FIG. 1. A single sensor in the exam room monitors the progress of the appointment. At time 311, the assistant (long-dash line 302) brings the patient (solid line 301) into the exam room. After some time taking vital signs and the like, assistant 302 leaves the exam room at time 321, leaving patient 301 in the exam room waiting for the physician. The physician (short-dash line 303) enters the exam room at time 331, performs the exam, and leaves at time 341.

Horizontal fine solid lines 311, 321, 331, 341 and 351 represent local times logged when actual entries or exits are detected. Therefore, they coincide with times at which the thicker lines representing the locations of physician 303, assistant 302, and patient 301, cross between the "Out of Exam Room" lane (i.e., out of the detection range of an exam-room sensor) and the "In Exam Room" lane (i.e., in the detectable range of the exam-room sensor). By contrast, horizontal fine dotted lines 310, 320, 330, and 340 represent the scheduled entry and exit times. These times are stored in advance when the day's schedule is prepared, then retrieved to calculate a delay after each corresponding actual entry or exit occurs. For example, assistant 302 was scheduled to escort the patient into the exam room at time 310, but did not actually do so until time 311; the appointment is already running behind schedule.

In this example, delays propagate: every subsequent delay is either the same length or longer than the immediately previous delay. Besides computing the delay between the scheduled and actual events, some embodiments of the process compare the delay to a stored threshold 305. Thresholding prevents excess notifications of employee and patient devices when the delay is deemed too small to cause patients of employees to change his or her plans. Digital clocks can measure delays of tiny fractions of a second, but humans, depending on the situation, may consider delays of less than a few minutes—or even delays of less than ½ hour—too small to warrant rescheduling the appointment. Setting a threshold 305 allows employees and upcoming patients to go about their day without being distracted by alerts about delays too small to cause concern.

Figure 4A:
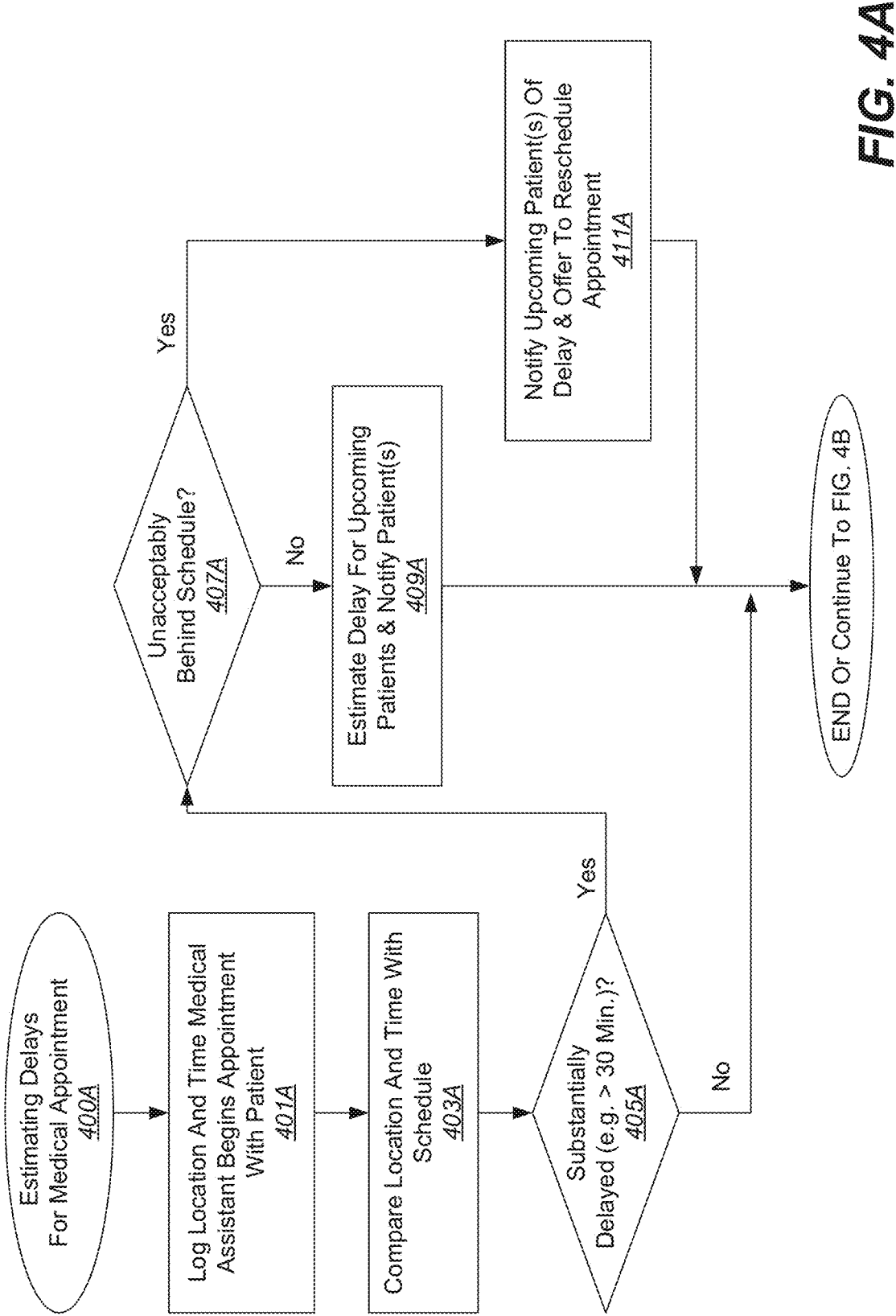
FIGS. 4A-4C are flow sequences illustrating one example of a process for estimating delays for a medical appointment.
Figure 4B:
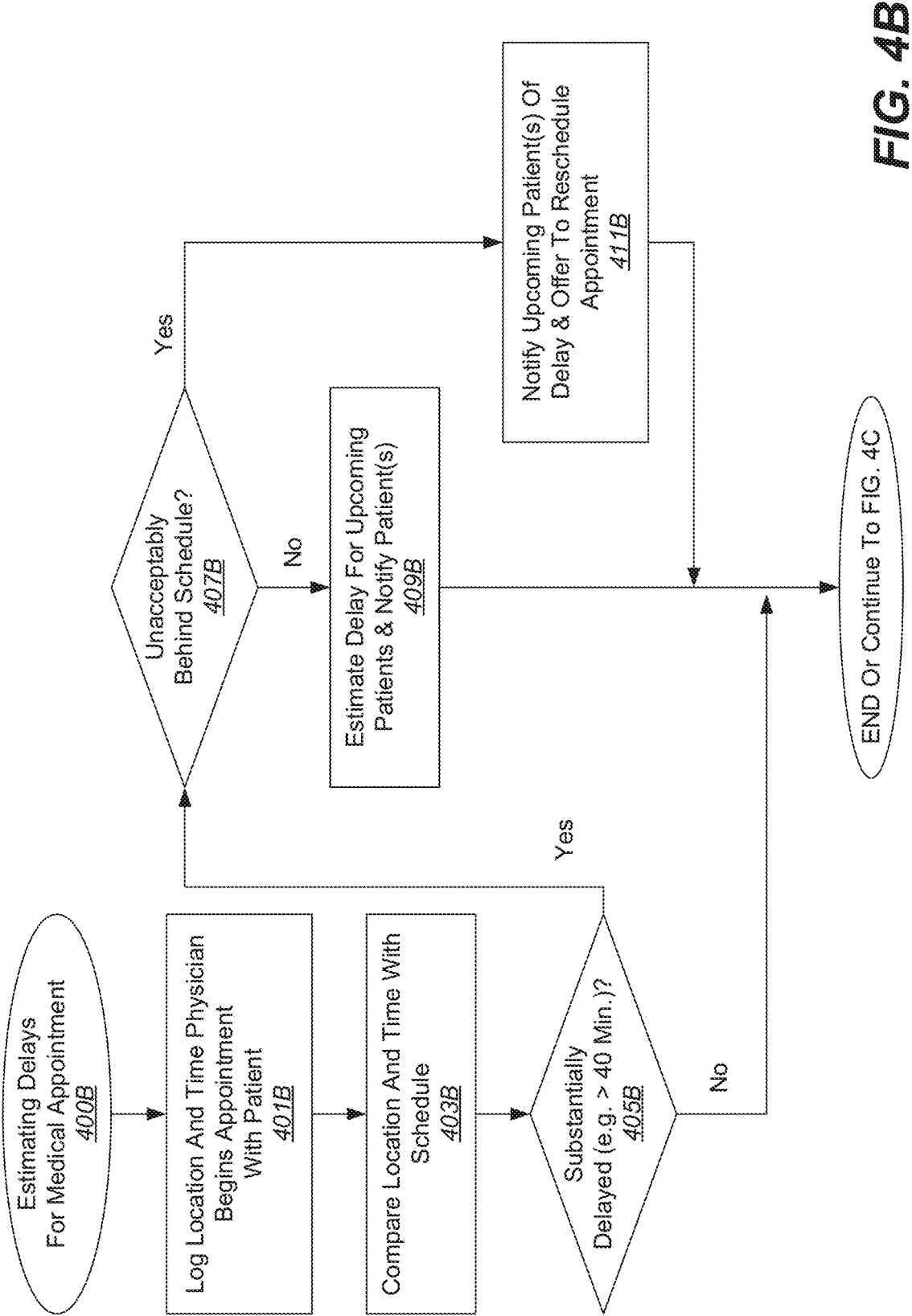
Figure 4C:
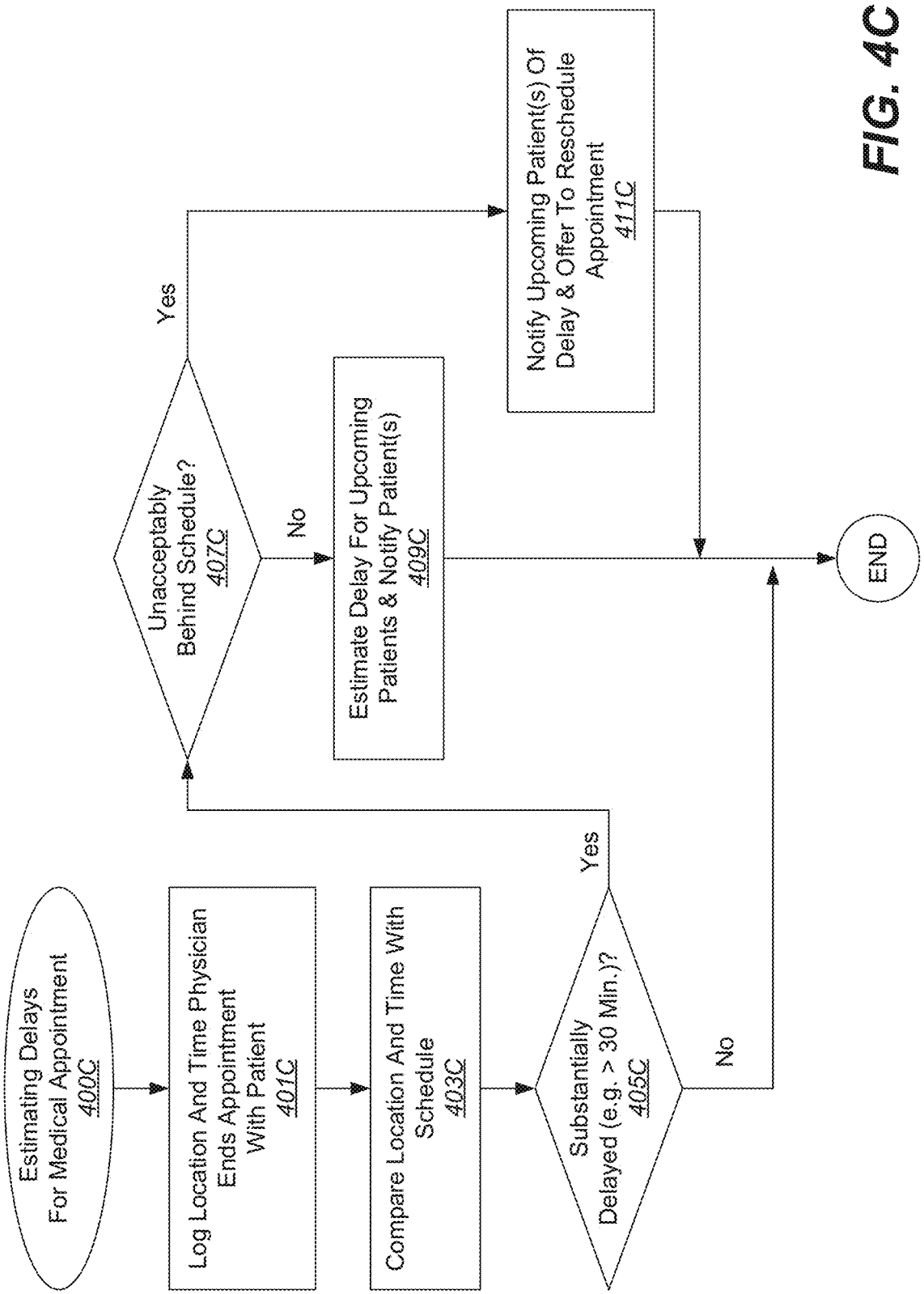

FIGS. 4A-4C illustrate examples of flow sequences of processes for estimating delays for a medical appointment. The processes shown in each of the figures can be used alone or together, depending on the application. For instance, the process shown in FIG. 4A can be used alone in some examples, whereas, FIGS. 4A-4C can be combined in other examples. In some aspects, the notification system can be viewed as a virtual waiting room. The system tracks when appointments are running late and the system informs an upcoming patient that their appointment is delayed and that they should delay arrival by a certain amount of time.

With reference to FIG. 4A, shown is a flow sequence illustrating one example of a process for estimating delays for a medical appointment. In this example, delays in the schedule are estimated based on the time that a medical assistant (or nurse) begins an appointment with a patient. According to various embodiments, scheduling times, activity and location tracking, event monitoring, and other triggers pertinent to maintaining on-time scheduled appointments are referred to herein as scheduling information. In this process, estimating delays for a medical appointment 400A begins with logging a location and time when a medical assistant begins an appointment with a patient at 401A. Next, this logged location and time is compared to a schedule at 403A. This schedule includes the patients and times for their appointments for the current day. Based on this comparison, a determination is made whether the appointment is on time or substantially delayed at 405A. For instance, if the time that the medical assistant begins the appointment is less than thirty (30) minutes later than the scheduled time for this patient, the appointment can be categorized as being on time and the process ends. If the time that the medical assistant begins the appointment is thirty (30) minutes or more past the scheduled time for this patient, then the appointment can be considered to be substantially delayed and the process continues at 407A. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 407. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled, any amount of time can be used depending on the particular application of the system. For instance, certain physicians may want to decrease this time based on their allotted examination times or to generally increase patient satisfaction.

In the current example, if the delay is less than two (2) hours, then delays for upcoming appointments are then estimated and these upcoming patients are notified of these delays at 409. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified.

According to various embodiments, upcoming patients are notified at 409A using their contact information. As described in more detail with regard to FIG. 11, this contact information can be stored in a database and accessed by the notification system. This contact information can be kept separate from patient medical records, in order to avoid any privacy concerns regarding the federal Health Insurance Portability and Accountability Act of 1996 (HIPAA) or similar medical privacy laws in other nations. Specifically, the notification system accesses the contact information for upcoming patients, such as a phone number. In some examples, the notification system sends a text message to the upcoming patients notifying them of the expected delay and a later time that they should arrive. For instance, an upcoming patient originally scheduled for a two o'clock appointment may receive the following message: "Dear Jane, your appointment originally scheduled for 4:00 pm today with Dr. Smith is running behind schedule. Could you please arrive at 4:45 pm instead? Sorry for the delay. Thank you for your understanding." Alternatively, the notification system can send a voicemail or email to upcoming patients, depending on factors such as the patients' contact preferences and the office infrastructure. According to various embodiments, scheduling information such as medical professional location tracking, appointment start triggers, event monitoring, etc., are cryptographically separated from HIPAA information.

According to various embodiments, medical professional activities, movements, and locations can be automatically or manually detected to allow improved appointment scheduling. For example, appointment start times can be manually or automatically triggered when a physician enters or a room and characteristics of the appointment can be used to determine whether later appointments need to be adjusted. In particular embodiments, mechanisms for tracking physician or other medical personnel activities, movements, and locations for scheduling appointments are firewalled from systems managing patient medical data. In some examples, different encryption mechanisms are used to encrypt HIPAA data and scheduling information so that access to one system does not permit access to another system. In other examples, different networks such as different virtual networks or different physical networks are used to transport the different types of data. According to various embodiments, patient medical data is encrypted during both storage and transmission using a different mechanism from medical personnel tracking data.

In the present example, if the delay is two (2) hours or more, then a determination is made whether some or all of the upcoming patients for the day need to be rescheduled. The patients that need rescheduling are then notified at 411A and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through the text message, email, or voice message. For instance, an interactive sequence can be presented to the patient to allow them to reschedule immediately. This can provide convenience for both the patients and the front office. Specifically, in some examples, one or more alternative times can be offered to the patient and the patient can select one. Once the patient is notified according to the described process (or if no delay is found), the process either ends or continues as described in FIG. 4B, depending on the desired application of the system.

With reference to FIG. 4B, shown is a flow sequence illustrating another example of a process for estimating delays for a medical appointment. In this example, delays in the schedule are estimated based on the time that a physician begins an appointment with a patient. This process can be used alone in some examples, or it can continue following the process described above with regard to FIG. 4A.

In the present example, estimating delays for a medical appointment 400B begins with logging a location and time when the physician begins an appointment with a patient at 401B. Next, this logged location and time is compared to a schedule at 403B. This schedule includes the patients and times for their appointments for the current day. Based on this comparison, a determination is made whether the appointment is on time or substantially delayed at 405B. For instance, if the time that the physician begins the appointment is less than thirty (30) minutes later than the scheduled time for this patient, the appointment can be categorized as being on time and the process ends. If the time that the physician begins the appointment is thirty (30) minutes or more past the scheduled time for this patient, then the appointment can be considered to be substantially delayed and the process continues at 407B.

Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 407B. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled in the present example, any amount of time can be used depending on the particular application of the system. For instance, certain physicians may want to decrease this time based on their allotted examination times or to generally increase patient satisfaction.

In this example, if the delay is less than two (2) hours, then delays for upcoming appointments are then estimated and these upcoming patients are notified of these delays at 409B. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified. In some examples, if multiple factors are used to determine schedule delays, such as the time that the medical assistant begins the appointment and the time that the physician begins the appointment, then only one notification may be provided. For instance, a step can be included that determines whether a notification has already been sent to this patient, and if so, then an additional notification will not be sent. In other examples, updates to this notification with current waiting times and real-time appointment adjustments can be made as updated delays are predicted.

According to various embodiments, upcoming patients are notified at 409 using their contact information. As described in more detail with regard to FIG. 11, this contact information can be stored in a database and accessed by the notification system. This contact information can be kept separate from patient medical records, in order to avoid any privacy concerns regarding the federal Health Insurance Portability and Accountability Act of 1996 (HIPAA).

Specifically, the notification system accesses the contact information for upcoming patients, such as a phone number. In some examples, the notification system sends a text message to the upcoming patients notifying them of the expected delay and a later time that they should arrive. For instance, a patient later in the day scheduled for a two o'clock appointment may receive the following message:

"Dear Jane, your appointment originally scheduled for 2:00 pm today with Dr. Smith is running behind schedule. Could you please arrive at 2:45 pm instead? Sorry for the delay. Thank you for your understanding." Alternatively, the notification system can send a voicemail or email to upcoming patients, depending on factors such as the patients' contact preferences and the office infrastructure.

In the present example, if the delay is two (2) hours or more, then a determination is made whether some or all of the upcoming patients for the day need to be rescheduled. The patients that need rescheduling are then notified at 411B and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through the text message, email, or voice message. For instance, an interactive sequence can be presented to the patient to allow them to reschedule immediately. This can provide convenience for both the patients and the front office. Specifically, in some examples, one or more alternative times can be offered to the patient and the patient can select one. Once the patient is notified according to the process (or if no delay is found), the process either ends or continues as described in FIG. 4C, depending on the desired application of the system.

In the present example, although both a location and time are logged when the physician begins the appointment, it should be noted that in some embodiments, the location need not be logged. For instance, if the patient and time are adequately identified and logged, then the location does not need to be logged in order to compare the actual appointment time with the scheduled appointment time. According to various examples, the location log can be used to determine when a physician is seeing a particular patient. Specifically, in cases where location logging is automated, such as with sensors, GPS, or the like, then the location can provide information about which patient a physician is currently seeing.

With reference to FIG. 4C, shown is a flow sequence illustrating another example of a process for estimating delays for a medical appointment. In this example, delays in the schedule are estimated based on the time that a physician ends an appointment with a patient. This process can be used alone in some examples, or it can continue following the process described above with regard to FIGS. 4A and/or 4B.

In the present example, estimating delays for a medical appointment 400C begins with logging a location and time when the physician ends an appointment with a patient at 401C. Next, this logged location and time is compared to a schedule at 403C. This schedule includes the patients and times for their appointments for the current day. Based on this comparison, a determination is made whether the appointment is on time or substantially delayed at 405C. For instance, if the time that the physician ends the appointment is less than thirty (30) minutes later than the scheduled time for this patient plus the allotted duration of this type of appointment, the appointment can be categorized as being on time and the process ends. If the time that the physician ends the appointment is thirty (30) minutes or more past the scheduled time for this patient plus the allotted duration of this type of appointment, then the appointment can be considered to be substantially delayed and the process continues at 407C. Although thirty (30) minutes is used in this example to determine whether the appointment is on time, any amount of time can be used. In some examples, this amount of time can be set by a particular medical professional based on their preferences and office procedures.

In the present example, if the appointment is delayed thirty (30) or more minutes, a determination is then made whether the appointment is unacceptably behind schedule at 407C. For the sake of this example, two (2) hours is used as a measure of when an appointment is unacceptably behind schedule. Appointments unacceptably behind schedule will not leave enough time for upcoming appointments, and consequently, will require that the upcoming appointments be rescheduled. Although two (2) hours delay is used as the threshold for determining when upcoming appointments need to be rescheduled in the present example, any amount of time can be used depending on the particular application of the system. For instance, certain physicians may want to decrease this time based on their allotted examination times or to generally increase patient satisfaction.

In this example, if the delay is less than two (2) hours, then delays for upcoming appointments are then estimated and these upcoming patients are notified of these delays at 409C. For these upcoming patients, the delay is between thirty (30) minutes and two (2) hours based on the current patient. In some examples, the delay can be propagated through the schedule equally. Specifically, if the current appointment is behind forty (40) minutes, then all of the upcoming appointments can be shifted forty (40) minutes later. However, in some examples, each subsequent appointment can be shifted a certain amount in addition to this forty (40) minutes if the system estimates that the physician will incur additional delays from the subsequent appointments. Once the delay is estimated for the upcoming patients, the patients are then notified. In some examples, if multiple factors are used to determine schedule delays, such as the time that the medical assistant begins the appointment and/or the time that the physician begins the appointment, then only one notification may be provided. For instance, a step can be included that determines whether a notification has already been sent to this patient, and if so, then an additional notification will not be sent. In other examples, updates to this notification with current waiting times and real-time appointment adjustments can be made as updated delays are predicted.

According to various embodiments, upcoming patients are notified at 409C using their contact information. As described in more detail with regard to FIG. 11, this contact information can be stored in a database and accessed by the notification system. This contact information can be kept separate from patient medical records, in order to avoid any privacy concerns regarding the federal Health Insurance Portability and Accountability Act of 1996 (HIPAA).

Specifically, the notification system accesses the contact information for upcoming patients, such as a phone number. In some examples, the notification system sends a text message to the upcoming patients notifying them of the expected delay and a later time that they should arrive. For instance, an upcoming patient scheduled for a two o'clock appointment may receive the following message: "Dear Jane, your appointment originally scheduled for 2:00 pm today with Dr. Smith is running behind schedule. Could you please arrive at 2:45 pm instead? Sorry for the delay. Thank you for your understanding." Alternatively, the notification system can send a voicemail or email to upcoming patients, depending on factors such as the patients' contact preferences and the office infrastructure.

In the present example, if the delay is two (2) hours or more, then a determination is made whether some or all of the upcoming patients for the day need to be rescheduled. The patients that need rescheduling are then notified at 411C and are offered an opportunity to reschedule their appointments. For instance, if the physician is behind two hours, but can cancel two upcoming appointments and be back on schedule with subsequent patients, these two appointments may need to be rescheduled. In some cases, the schedule can be rearranged to cause as few reschedules as possible. In some examples, the option to reschedule can be offered through a text message, email, voice message, or push notification. For instance, an interactive sequence can be presented to the patient to allow them to reschedule immediately. This can provide convenience for both the patients and the front office. Specifically, in some examples, one or more alternative empty appointment time slots can be offered to the patient and the patient can select one. Once the patient is notified according to the process described (or if no delay is found), the process ends.

In the present example, although both a location and time are logged when the physician ends the appointment, it should be noted that in some embodiments, the location need not be logged. For instance, if the patient and time are adequately identified and logged, then the location does not need to be logged in order to compare the actual appointment time with the scheduled appointment time. According to various examples, the location log can be used to determine when a physician is seeing a particular patient. Specifically, in cases where location logging is automated, such as with sensors, GPS, or the like, then the location can provide information about which patient a physician is currently seeing.

In some embodiments, multiple processes described with regard to FIGS. 4A-4C can be used to provide feedback to the physician about schedule efficiencies or inefficiencies. For instance, data can be gathered and statistics can be generated for a particular day showing how many appointments were delayed, by how much, and whether the delays were caused by medical assistant delay, physician delay, or appointments that ran longer than the allotted time for the type of exam that was performed. In addition, statistics can be provided over periods of times, from days to months to years, depending on the time specified. In some examples, graphs and/or charts can be provided that show trends. Furthermore, suggestions can be provided based on the data provided, such as whether actual examination times are exceeding the allotted times, and by how much. Percentages can be provided showing how much overrun is occurring and how often. Suggestions such as extending the allotted times for examinations or spacing appointments further apart may be provided.

Figure 5:
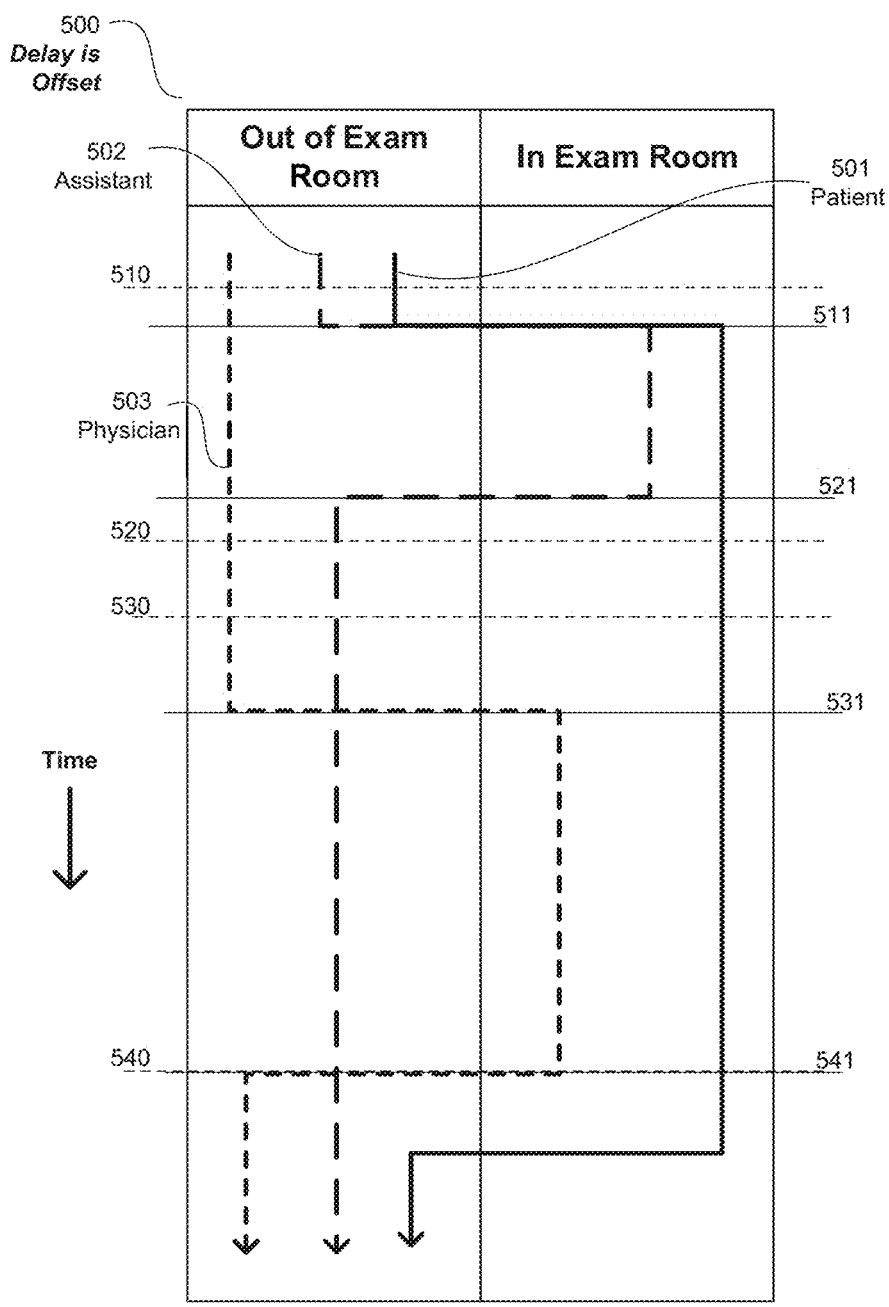
FIG. 5 is a swim-lane diagram of compensated delays of appointments.

With reference to FIG. 5, shown is a swim-lane diagram of compensated delays in appointments. FIG. 3, discussed above, illustrated propagating delays; for successive entries or exits, the delay either remained constant or increased. Delays may not always propagate, however; a delay may be "made up" if a process takes less than the expected time (e.g., a patient arrives with a questionnaire already filled out) or is cancelled altogether (e.g., if a patient "noshows" or reschedules only a few hours before the appointment). Assistant 502 is scheduled to bring patient 501 to the exam room. at time 510, but does not actually do so until later time 511; the appointment is running behind schedule. After some time taking vital signs and the like, assistant 502 is scheduled to leave the exam room at time 520, but does so at earlier time 521 so that now the appointment is ahead of schedule. Physician 503) is scheduled to enter the exam room at time 530, but does not do so until later time 531, so that the appointment is behind schedule again. However, physician 503 leaves the exam room at time 541, which is equal to scheduled time 540, putting the appointment back on schedule.

The following appointment (and, barring further delays, the appointments following it) may actually start on time. Meanwhile, though, a delay message may have been transmitted at time 511 (or possibly not if this small delay was sub-threshold. Depending on the embodiment, a "back-on-schedule" notification might have been transmitted at time 521, or the system may be programmed to ignore on-schedule events. Another delay message may have been transmitted at time 531 (a longer delay likely to exceed the threshold) and perhaps one or more patients decided to reschedule, but at time 541 there was no longer a delay, therefore no actual need to incur the added overhead of the rescheduling.

Identification of gating events can smooth out such fluctuations in expected delays. After leaving the exam room at time 541, physician 503 is now free to see another patient (or will be after an allotted time to "wrap up" the current appointment). Thus the physician's exit from the exam room at time 541 may be the "gating event" that determines the end of the appointment, making it possible to estimate the beginning of the next appointment. Therefore, in some embodiments the system may log all entries and exits, with or without comparing the logged time with the scheduled time, but it may refrain from transmitting delay messages except when a gating event occurs.

Figure 6:
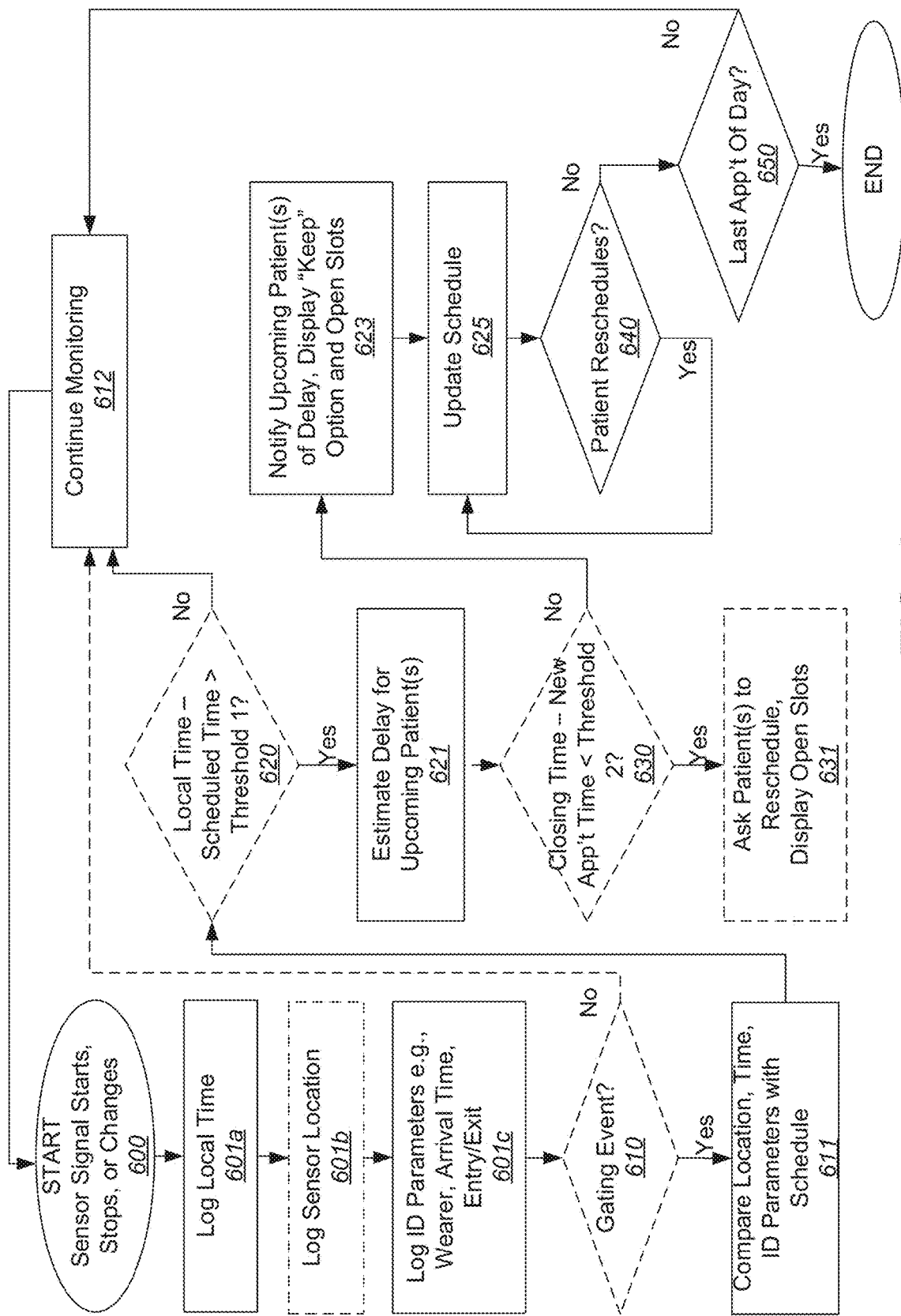
FIG. 6 is a flow sequence illustrating another example of a process for estimating delays for a medical appointment.

With reference to FIG. 6, shown is a flow diagram of an operation that may be implemented as software. Operation 600 may include detecting a position or motion of a first identifier within a sensor range, wherein the sensor range at least partially covers a first service location. A change in the sensor signal, which may include being turned on or off, triggers operations 601*a-c*, which may include logging a local time 601*a*, optionally logging a sensor location 601*b* (e.g., if there are multiple sensors to distinguish or the sensor moves from one service location to another), and logging a first identifying parameter of the first identifier (to identify the particular wearer) in response to an entry of the first identifier into the sensor range or an exit of the first identifier out of the sensor range.

Optional decision 610 may include determining whether the logged entry or exit is a gating event. If so, or if the gating-event determination is omitted, operation 611 may include retrieving a scheduled time of the entry or the exit during a first appointment and subtracting the first scheduled time from the local time to estimate a first delay.

Optional decision 620 may include comparing the first delay to a threshold. If the first delay is greater than the threshold, operation 621 may include estimating the delay of upcoming patients' appointments by adding the first delay to the second scheduled time to compute the expected time of the delayed appointment. Operation 623 may include notifying a first device that the second appointment will be delayed until the expected time and optionally display a selectable "keep" option and a selectable list of open appointment slots on the first device after the notifying. The device may be an employee device, an upcoming patient's device, or both. Selection may be done by typing, touching, clicking, voice, or any other suitable way to choose from a set of options using the device.

Optional decision 630 may calculate whether the delayed time of the day's last appointment has become so late that the office will close before the appointment is completed. If so, the holder of that appointment may be offered rescheduling options but no "keep" option in operation 631. Operation 625 updates the stored schedule for the rest of the day to account for the currently expected delay. The system may respond to an upcoming patient's selection of a "keep" option by replacing the patient's current scheduled time with the expected time of the delayed appointment. Decision 640 determines whether an upcoming patient has rescheduled and, if so, executes an updating operation 625 replacing the patient's currently scheduled appointment with the rescheduled appointment. In some embodiments, this step may be executed any time any patient requests a reschedule, rather than only in response to a delay notification. Operation 612 returns the system to monitoring the sensor(s) whenever there is no reason for a delay notification, such as when the most recent event was not a gating event per decision 610 or was not an above-threshold delay per decision 620. Finally, decision 650 determines whether the last appointment of the day has been finished; if so, the system responds by stopping the process, ceasing to monitor the sensor(s)

FIGS. 7A-7C illustrate examples of delay notifications displayed on device screens. Non-display notifications such as voice-mails are also within the scope of some embodiments.

With reference to FIG. 7A, shown is a cell phone displaying a text message. Most cell phones 701 are able to display a text message 703, which may include details 705 of open appointment slots for rescheduling and enable the user to communicate a choice using the keypad.

With reference to FIG. 7B, shown is a smartphone displaying a push notification from an installed application ("app"). A smartphone 711 may also receive voicemail and text messages, but may include the additional possibilities of push notifications 713 or dedicated apps with graphic user interfaces (GUIs). A GUI may display "Keep" option 715 and open slots 717 as buttons or other clickable or touchable features.

With reference to FIG. 7C, shown is a desktop computer displaying an alert. As well as upcoming patients, employees of the medical office can also benefit from delay notifications by organizing their tasks and breaks around the times when the appointments are likely to begin and end, rather than when the appointments were originally intended to begin and end.

Figure 8:
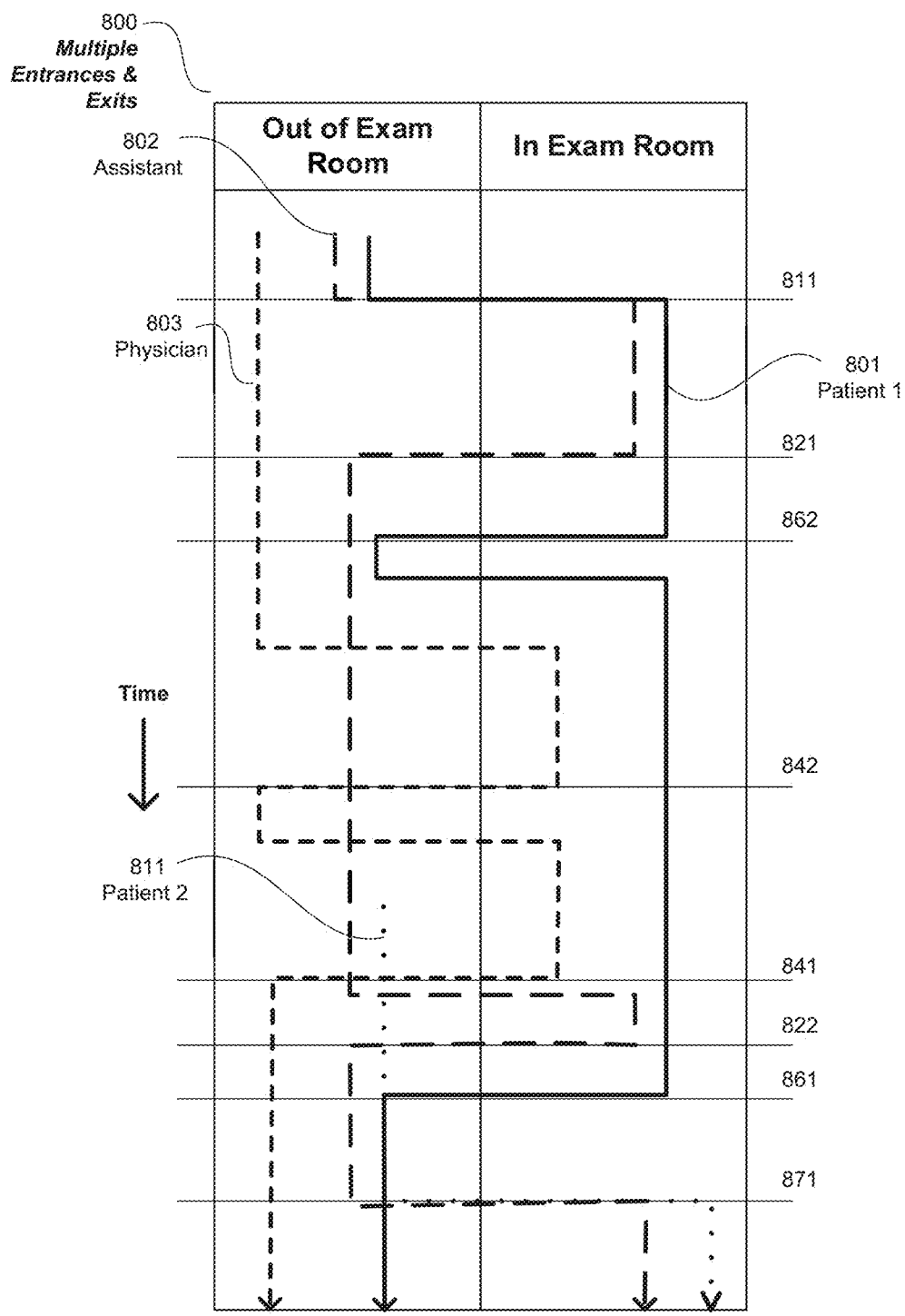
FIG. 8 is a swim-lane diagram of multiple entries and exits of the same individuals to and from an examination room in the course of a single appointment.

With reference to FIG. 8, shown is a swim-lane diagram of multiple entries and exits of participants in a single appointment. Previously it was proposed that the physician's exit from the exam room might be the best indicator of the appointment being over, and therefore a good choice of a gating event. However, if the physician exits the exam room more than once during a single appointment, only the last such exit is preferably used to calculate the delay.

For example, physician 803 exits the exam room at time 842, but only temporarily. Physician 803 may need to answer an urgent question, fetch an injectable, or the like. Shortly thereafter, physician 803 re-enters the exam room, finishes his or her part of the appointment, and re-exits at time 841. Meanwhile, the sensor detects exit 842 and may compute and communicate a delay based on exit time 842. Upon detecting the second exit 841, the system may compare the local time with the NEXT scheduled physician-exit time during the following appointment, which will yield an inaccurate result.

Likewise, assistant 802 may enter the exam room at time 811, collect preliminary information for the physician, and leave at time 821, then enter again to answer logistics questions for an upcoming procedure after the physician exits, and exit again at time 822. If this happens in some types of appointments but not in others, some systems might choose the wrong scheduled time to compare to the second exit.

Patient 801's exit from the exam room might be a better choice of gating item; the sensor would detect patient 801's exit at time 861, then retrieve the log entry for the immediately preceding physician 803 exit at time 841 and calculate the delay from it. In this process, the patient's exit is a "confirming event" signaling that the appointment is over and the physician's most recent exit is therefore the gating event. However, even patient 801 does not necessarily stay in the exam room for the entire appointment. For example, the patient may exit at time 862 to give a sample or answer an administrative question, and then return to the appointment.

Looking further ahead, patient 801's appointment must definitely be over when the next patient 811 enters the exam room at time 871. Therefore, a system can avoid being "confused" by multiple entries and exits of participants in a single appointment by using the entry of the next patient as a confirming event, retrieving the most recent physician exit before time 871, and using it to calculate the delay. This prevents patient 811 from getting updates on delays generated during patient 801's appointment. However, because those updates would likely have been excessively short notice for patient 811 to change plans, the impact is minimal.

Figure 9:
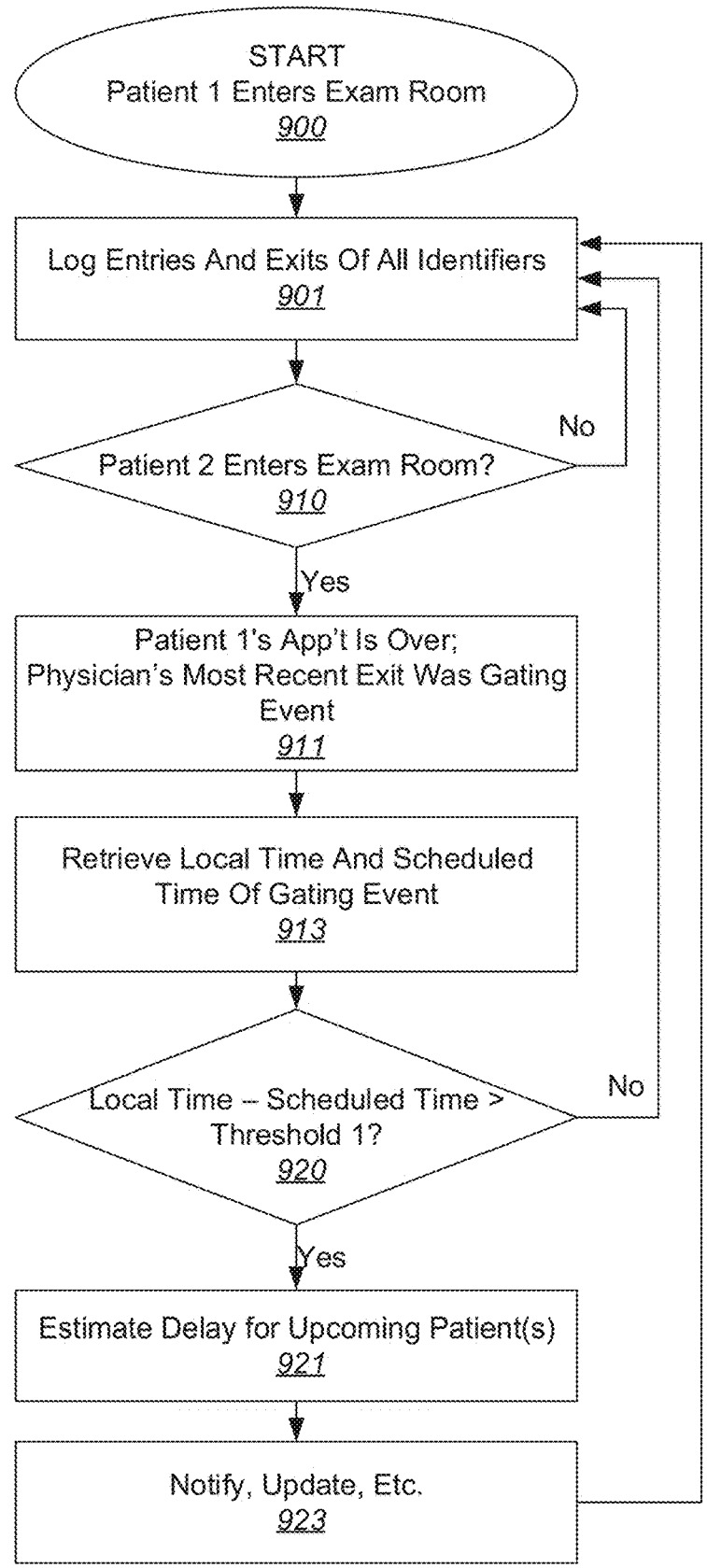
FIG. 9 is a flow sequence illustrating another example of a process for estimating delays for a medical appointment.

With reference to FIG. 9, shown is a flow diagram of a process accommodating multiple entries and exits. An appointment begins with operation 900 with a first patient entering the exam room. Operation 901 may include logging entries and exits detected by the sensor.

After each logging operation, the system decides at decision 910 whether the most recent event confirms that the first patient's appointment has ended. In this example, the confirming event is the entry of a second patient into the exam room. If not, the system may return to operation 910 of monitoring and logging, rather than performing delay calculations. If so, operation 911 may include identifying the most recent event as a confirming event, therefore the last previous physician exit was the gating event. Operation 913 may include retrieving the local time and the scheduled time of the gating event. Decision 920 determines whether the difference between the gating event's local time and its corresponding scheduled time is greater than a stored threshold. If not, the system may return to operation 910 of monitoring and logging, rather than performing delay calculations. If so, operation 921 may include estimating a delay for upcoming appointments, followed by operation 923 of notifying devices, offering reschedule options, and updating the schedule.

FIGS. 10A-10C illustrate an embodiment in which a patient carries a sensor and the service locations, physicians, and assistants carry active beacons. This type of system tracks the service locations that a patient visits—helpful in practices where patients spend time in treatment rooms, sample collection rooms, the physician's office or conference room, or elsewhere besides an exam room. The system also tracks the time that physicians and assistants spend in proximity to the patient, which may be helpful in settings where patients are examined, tested, or treated in cubicles or bays or at counters that are small and close together with partial dividing walls or none at all.

With reference to FIG. 10A, shown is an example of a medical office floor plan. Optionally, when patient 1001 checks in at reception 1010, office staff member 1006 may use machine 1016 to program an identifying parameter into sensor 1013 that is unique to the patient or the appointment. Sensor 1013 has a sensor range 1043 which in some embodiments may be only 1-2 m (3-6') and a built-in clock 1015 or access to some other clock signal.

Assistant 1002 wears beacon 1021 emitting signal 1026, which is detected by sensor 1013 when assistant 1002 escorts patient 1001 to exam room 1020. In some embodiments, signal 1026 may include an identification parameter associated with the assistant wearing it. When patient 1001 enters exam room 1020, sensor 1013 detects exam-room beacon signal 1024 from exam-room location beacon 1022. Signal 1024 may also include an exam-room identification parameter. When assistant 1002 exits the exam room, sensor 1013 stops detecting signal 1026 but continues detecting signal 1024 because patient 1001 is still in exam room 1020.

Meanwhile, physician 1003 in office 1030 wears physician's beacon 1031 transmitting physician's beacon signal 1033 while office location beacon 1023 transmits office beacon signal 1034. When physician 1003 enters exam room 1020, sensor 1013 will begin to detect physician's beacon signal 1033. If physician 1003 then escorts patient 1001 into office 1030 for a conference, sensor 1013 will stop detecting exam-room beacon signal 1024 and begin detecting office beacon signal 1034.

In some embodiments, patient 1001 may return sensor 1013 to member of office staff 1006 when the appointment ends. The timing information logged by sensor 1013 may be uploaded to storage via machine 1016 or some other device. Note that this approach may obviate the need for gating-event and confirming-event capture and the accompanying calculations; when the patient returns sensor 1013, the appointment may be over by definition. Optionally, delay data over a span of time such as a week or a month may be analyzed to diagnose any frequent causes of delay.

With reference to FIG. 10B, shown is a display interface 1051 for programming a patient sensor at the beginning of an appointment. The patient's record number, name, and/or appointment time may be used to identify the log entries uploaded later. The patient arrival time may help derive how many and what lengths of delays are generated when patients arrive late.

With reference to FIG. 10C, shown is a display interface 1052 for uploading data on patient entry and exit times a patient sensor at the beginning of an appointment. Any or all of identifying parameters 1054 may be used to label the data in a database.

Figure 11:
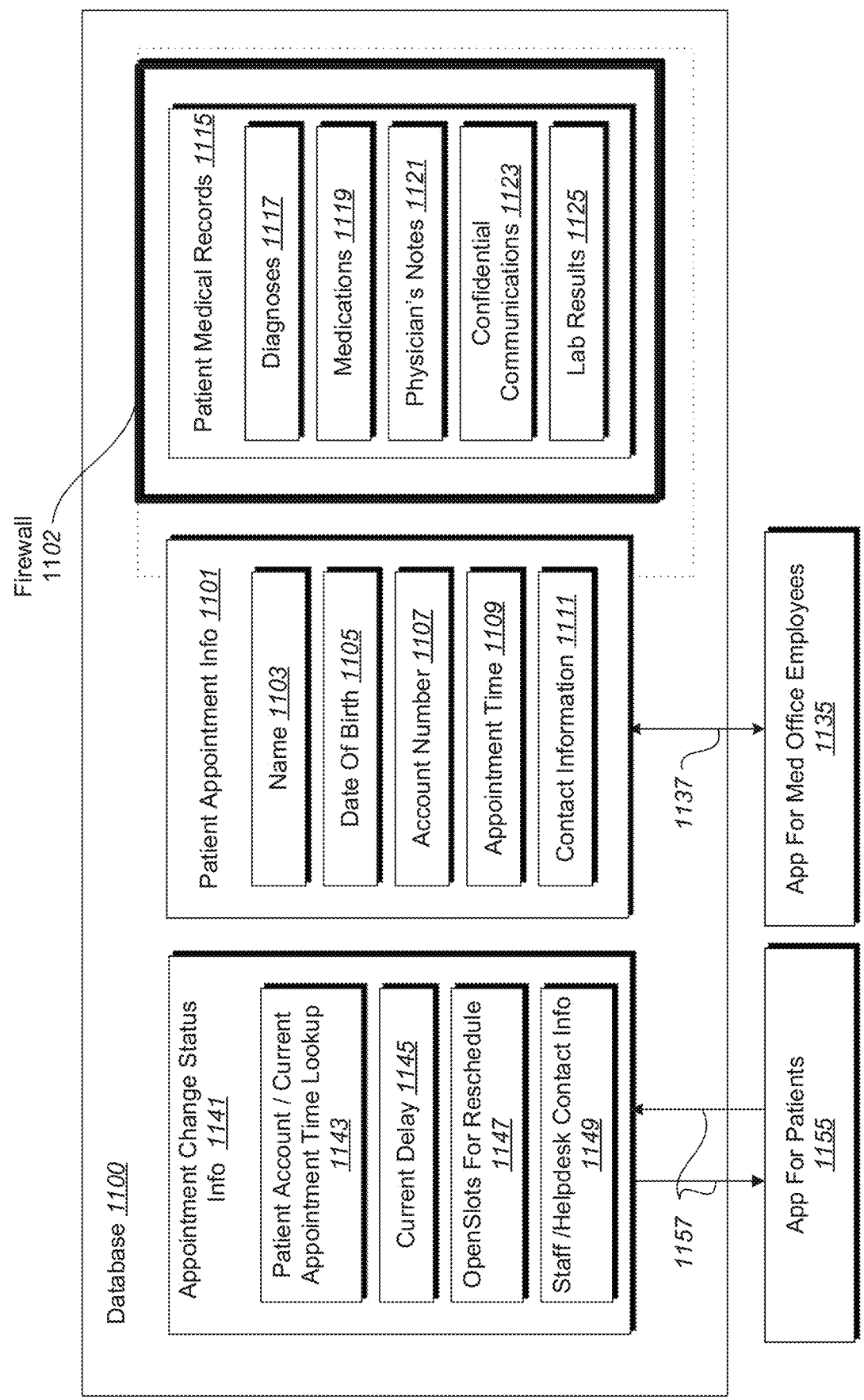
FIG. 11 is a diagrammatic representation of one example of a database designed to store patient information.

With reference to FIG. 11, shown is a diagrammatic representation of one example of a database designed to store patient information. As described above with regard to FIGS. 4A-4C, contact information for patients is retrieved by the notification system when upcoming patients are to be notified of a delay in their appointment times. However, in order to avoid any privacy concerns regarding HIPAA, the notification system is limited to retrieving contact information that is not related to patient-sensitive information.

In the present embodiment, database 1100 includes patient appointment information 1101 and patient medical records 1115. Patient appointment information 1101 includes information for numerous patients such as name 1103, date of birth 1105, account number 1107, appointment time(s) 1109, and contact information 1111. The contact information 1111 can include information such as phone number(s) (for text and/or voicemail), email address, mailing address, and residence address. Additional or different information can be included, depending on the intended use of the database. However, patient appointment information is intended to include information that can be accessed by a scheduling or front office, without concerns about privacy under HIPAA. For example, patient appointment information 1101 may be accessed by an app 1135 on office-employee devices over a network 1137.

In some embodiments, appointment change status information 1141 may be stored in the non-HIPAA portion of the same database 1100. Appointment change status information 1141 may include, without limitation, lookup table 1143 of the latest appointment times held by each patient; current delay information 1145 collected by sensors; available open slots 1147 for patients who opt to reschedule their appointments; and contact info for patients who need help with appointment schedule issues. Appointment change status information 1141 may be accessed by an app 1155 on patients' devices over a network 1157, which may or may not be the same as network 1137. In some embodiments, patients' option choices (e.g., to keep a delayed appointment or to reschedule) are received in database 1100 over network 1157.

In the present example, patient medical records 1115 are protected by a firewall 1102 that prevents inadvertent or unauthorized access to patient information protected under HIPAA. The patient medical records 1115 include information for numerous patients such as diagnoses 1117, medications 1119, physician's notes 1121, confidential communications 1123, and lab results 1125. Additional or different information can be included depending on the preferences of the physician or practice. The patient medical records 1115 may include sensitive information that is protected under HIPAA privacy laws. Accordingly, this information must be handled carefully and access to it must be restricted to authorized people and systems.

According to various embodiments described herein, a medical scheduling management system notifies upcoming patients of a delay in their appointment times by accessing patient appointment information such as name 1103, appointment time 1109, and contact information 1111. In some examples, the notification system is implemented as an app for mobile devices. This app 1135 retrieves 1137 patient appointment information to predict schedule delays, such as by retrieving appointment times 1109 and comparing these appointment times 1109 to real-time appointment progress for a particular physician. In addition, this app 1135 retrieves contact information 1111 and names 1103 for patients that are to be notified of upcoming schedule delays. As indicated in the figure, the app 1135 does not have access to patient medical records 1115, and is prevented from accessing these patient medical records 1115 by firewall 1102. Although this example is described in the context of an app that can be implemented on one or more smartphones, mobile devices, etc., it should be recognized that this notification system can be implemented over any computer system. For instance, an office-based computer system can be updated manually by a medical assistant or other personnel to reflect current appointment times and the system can operate without any mobile devices.

Figure 12:
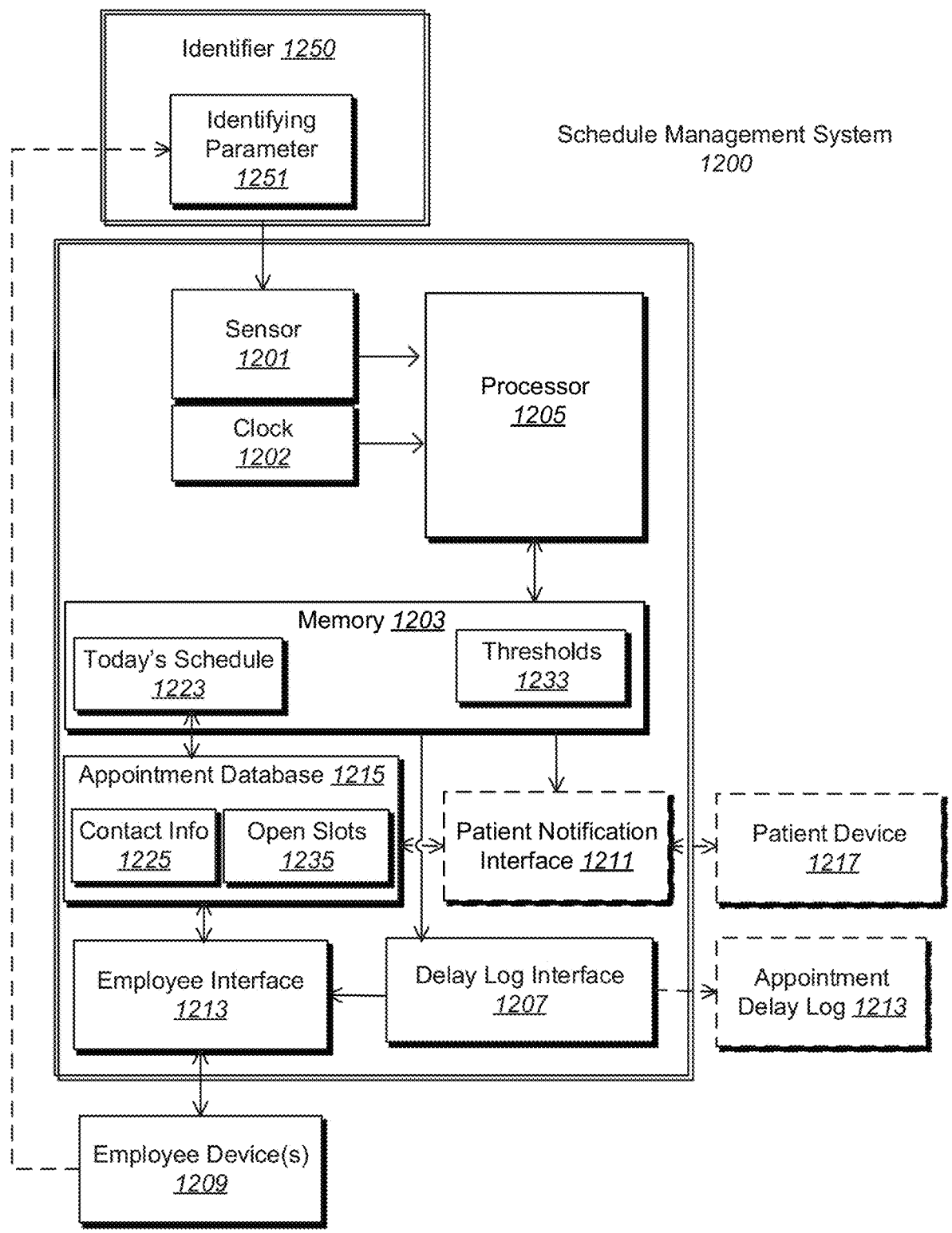
FIG. 12 is a diagrammatic representation of one example of a medical scheduling management system.
Figure 13:
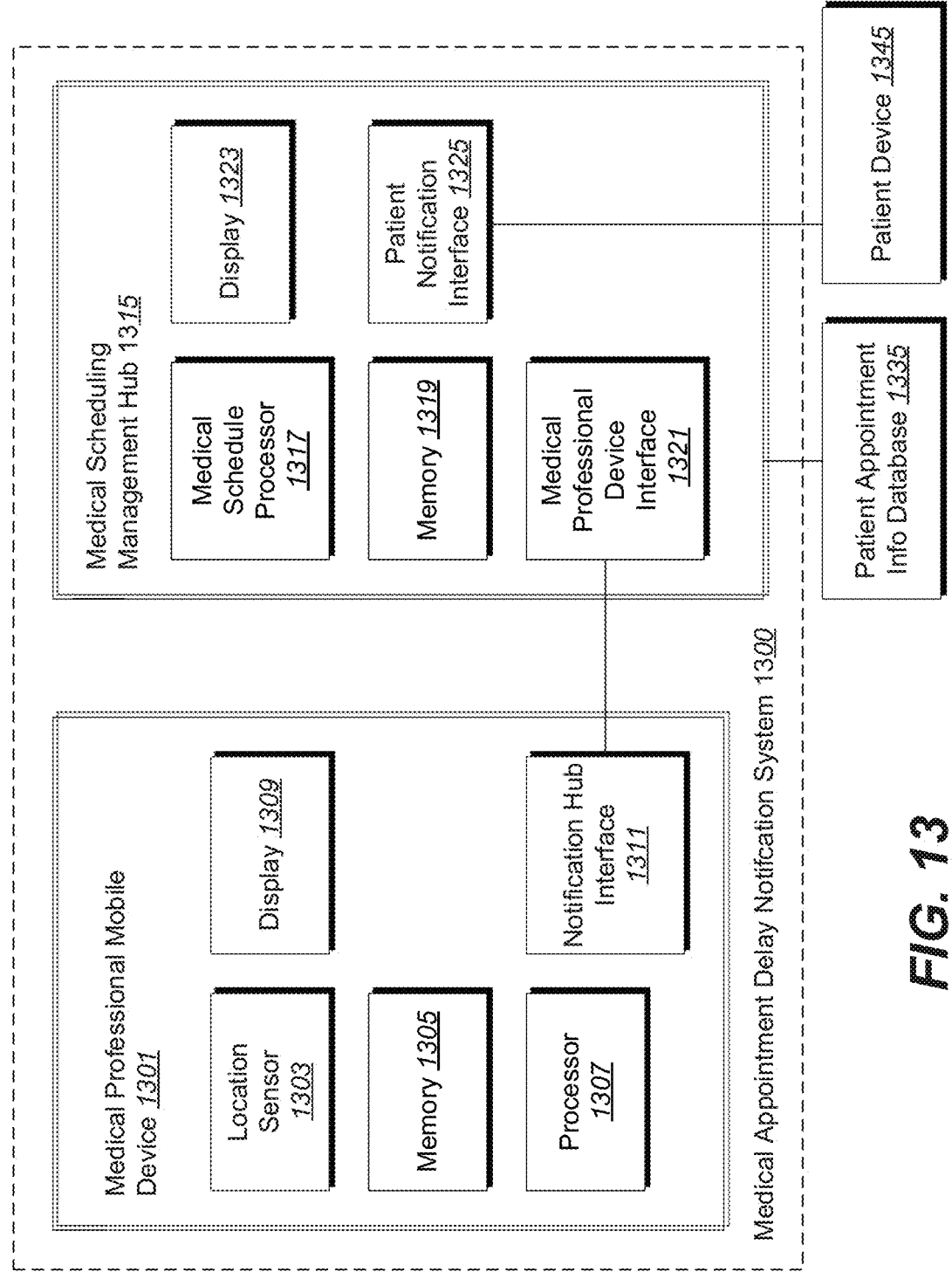
FIG. 13 is a diagrammatic representation of another example of a medical scheduling management system.

As described in previous examples, a medical scheduling management system can be used to predict delays for upcoming appointments and notify upcoming patients of these delays. The medical scheduling management system can be implemented in various ways. FIGS. 12 and 13 illustrate two examples of configurations for medical scheduling management systems. It should be noted that although two particular examples are described, modifications and adjustments can be made within the scope of this disclosure.

With reference to FIG. 12, shown is a diagrammatic representation of one example of a medical scheduling management system. The medical scheduling management system 1200 shown includes identifier 1250, location sensor 1201, clock 1202, memory 1203, medical schedule processor 1205, delay log interface 1207, employee interface 1213, employee device(s) 1209, and patient notification interface 1211. The location sensor 1201 is designed to detect when a medical professional enters an examination room to conduct an examination of a particular patient. Clock 1202 tracks the local time that is captured by processor 1205 when sensor 1202 detects the appearance or disappearance of an identifier. This location sensor 1201 can be implemented in numerous ways. In one example, a medical professional wears an identifier 1250 that is detectable in different areas of the office. The system is able to detect when identifier 1250, such as an RFID, etc. is in proximity to the location sensor. In some applications, there may be multiple identifiers simultaneously detected by a sensor. The processor, by extracting identifying parameter 1251, can discern whose identifier was detected by sensor 1201. In some applications, there may be multiple location sensors in the system.

In other examples, the location sensor 1201 represents an input interface used by a medical assistant or other personnel to enter the location of the medical professional at a particular time. Specifically, location and time information can be entered manually into the system. In some instances, the location sensor 1201 represents an input interface used by the medical professional to indicate when a particular appointment has started. Specifically, location and time information can be entered manually into the system. For instance, the next scheduled appointment may pop up or be otherwise selectable on a mobile device, and when the medical professional selects a button, the time is logged and this time is compared with the scheduled time. In yet other embodiments, the medical scheduling management system 1200 can be implemented as an app on a mobile device, such as a smartphone. In these examples, the location sensor 1201 can implement technologies such as GPS or other location sensing systems. In some examples, the location sensor 1201 can be omitted, such as when only the patients and times are logged.

In the present embodiment, the medical schedule processor 1205 is designed to log the time when a medical professional enters an examination room for a particular appointment and compare this time with a schedule to predict whether future appointments in the schedule will be delayed. The schedule typically includes patients and times for appointments scheduled on a particular day. According to various examples, the schedule may not include any HIPAA information. The memory 1203 is used to store data, which may include the present day's schedule 1223 and stored thresholds 1233, store program instructions, and maintain a local side cache. The program instructions may control the operation of an operating system and/or one or more applications, for example. In addition, display 1209 is used to allow a user to interact with the system, such as through a monitor, screen, etc.

In the present embodiment, the notification interface 1211 is used to notify upcoming patients if their appointments will be substantially delayed, as described in more detail with regard to FIGS. 4A-4C above. This notification interface 1211 is also designed to notify upcoming patients if their appointments need to be rescheduled. In some examples, the notification interface 1211 is also designed to provide an option for these patients to reschedule their appointments. As described above, the notification interface 1211 contacts a patient device 1217 using patient contact information such as a phone number, email, etc. In some examples, the notification interface 1211 notifies a patient via a text message. In other examples, the notification interface 1211 notifies a patient via a voicemail or email. Other notification modes can also be used, depending on the preferences of the patient and medical office.

In the present example, delay log interface 1207 allows data such as real-time location and time information for appointments in-progress to be transmitted to an appointment delay log 1213. This appointment delay log 1213 is located in a separate location that may be accessed by other devices. For instance, if the medical scheduling management system 1200 is implemented as an app on a mobile device, the appointment delay log 1213 may include an office computer that is accessible to office staff and personnel. In other examples, the appointment delay log 1213 can be located on a cloud drive. However, the delay log interface 1207 and appointment delay log 1213 can be omitted in some applications, depending on the needs of the practice.

As shown in the present embodiment, the medical scheduling management system 1200 can interact with a patient appointment information database 1215, such as the one shown and described with regard to FIG. 11. Patient appointment information database 1215 may include patient contact information 1225 and open appointment slots 1235. In particular, the medical scheduling management system 1200 accesses the patient appointment information database 1215 when predicting delays, when notifying upcoming patients by messaging their devices such as patient device 1217, and when notifying medical-office employees through employee interface 1213 via employee devices 1209. As mentioned with regard to FIG. 11, the information accessible in the patient appointment information database 1215 is not data that is protected under HIPAA.

With reference to FIG. 13, shown is a diagrammatic representation of another example of a medical scheduling management system. In this example, the medical scheduling management system 1300 includes a medical scheduling management hub 1315 and one or more medical professional mobile devices 1301. The medical professional mobile device 1301 can be implemented as a mobile device, such as a smart phone, tablet, etc. In other examples, this mobile device 1301 can be implemented as a wearable device such as a bracelet, fob, charm, clip, etc. As shown, the medical scheduling management hub 1315 is implemented on a computer such as a mobile device, office computer, server, etc. This serves as a "home base" for the system. In some examples, this hub 1315 is implemented on a central office computer or on the cloud.

In the present example, the medical professional mobile device 1301 includes a location sensor 1303, memory 1305, processor 1307, display 1309, and notification hub interface 1311. The location sensor 1303 is designed to detect when a medical professional enters an examination room to conduct an examination of a particular patient. This location sensor 1303 can be implemented in numerous ways. In one example, the location sensor is able to identify when the medical professional is in different areas of the office. In these examples, the location sensor 1303 can implement technologies such as GPS, RFID, Bluetooth, triangulation mechanisms, cameras, or other location sensing systems. In other examples, the location sensor 1303 represents an input interface used by the medical professional to indicate when a particular appointment has started. Specifically, location and time information can be entered manually into the system. For instance, the next scheduled appointment may pop up or be otherwise selectable the mobile device 1301, and when the medical professional selects a button, the time is logged and this time is compared with the scheduled time. In some embodiments, the location sensor 1303 can be omitted, such as when only patient and time information are logged.

In the present example, the medical professional mobile device 1301 includes memory 1305, which is used to store data and program instructions and maintain a local side cache. The program instructions may control the operation of an operating system and/or one or more applications, for example. In some examples, the size of the memory 1305 may be limited, as when most of the processing and storage of data is performed at the medical scheduling management hub 1315. In addition, the processor 1307 may include limited processing of the data collected. For instance, the data collected may include the times and locations of particular appointments, and the processor can be used to format the information before sending it to the medical scheduling management hub 1315. The limited memory 1305 and processor 1307 sizes and capabilities may be appropriate especially in cases when the medical professional mobile device 1301 is implemented as a wearable because the components can be smaller and more conveniently designed into a smaller casing to be comfortably worn. In the present example, display 1309 is used to allow the medical professional to interact with the system, such as through a screen, touch screen, etc. As described above, the medical professional may input data through this display 1309 and/or view options through the display.

In the present example, the medical professional mobile device 1301 also includes a notification hub interface 1311. This notification hub interface 1311 is used to communicate with the medical scheduling management hub 1315. In particular, data regarding real-time appointment start times are sent via the notification hub interface 1311 to the medical scheduling management hub 1315 via medical professional device interface 1321. In some examples, the medical professional device interface 1321 is used to send messages to the medical professional mobile device 1301 via the notification hub interface 1311, such as "Has the Smith 1:10 pm appointment begun?"

In the present embodiment, the medical scheduling management hub includes a medical schedule processor 1317 designed to log the time when a medical professional enters an examination room for a particular appointment and compare this time with a schedule to predict whether future appointments in the schedule will be delayed. The schedule typically includes patients and times for appointments scheduled on a particular day. According to various examples, the schedule does not include any HIPAA information. The memory 1319 is used to store data and program instructions and maintain a local side cache. The program instructions may control the operation of an operating system and/or one or more applications, for example. In addition, display 1323 is used to allow a user to interact with the system, such as through a monitor, screen, etc.

In the present embodiment, the patient notification interface 1325 is used to notify upcoming patients if their appointments will be substantially delayed, as described in more detail with regard to FIGS. 4A-4C above. This notification interface 1325 is also designed to notify upcoming patients if their appointments need to be rescheduled. In some examples, the notification interface 1325 is also designed to provide an option for these patients to reschedule their appointments. As described above, the notification interface 1325 contacts a patient 1345 using patient contact information such as a phone number, email, etc. In some examples, the notification interface 1325 notifies a patient via a text message. In other examples, the notification interface 1325 notifies a patient via a voicemail or email. Other notification modes can also be used, depending on the preferences of the patient and medical office.

As shown in the present embodiment, the medical scheduling management hub 1315 interacts with a patient appointment information database 1335, such as the one shown and described with regard to FIG. 11. In particular, the medical scheduling management hub 1315 accesses the patient appointment information database 1335 when predicting delays and when notifying upcoming patients, such as patient 1345. As mentioned with regard to FIG. 11, the information accessible in the patient appointment information database 1335 is not data that is protected under HIPAA.

Although FIGS. 12 and 13 describe particular configurations of medical scheduling management systems, it should be recognized that various configurations can be constructed within the scope of this disclosure. In addition, the system can be used to provide feedback to the physician and/or practice to allow them to generate physician/examination efficiency reports in some examples. For instance, the system can generate reports indicating the percentage of appointments that were delayed and by how much they were delayed. In some cases, the reports can be customizable to indicate factors such as whether certain types of appointments are delayed more often, times of day when more appointments are delayed, days of the week or month when appointments are delayed more often, etc. This feedback can be used by the physician to improve their care and service and become more efficient in their practice. This can lead to more satisfied patients, a more pleasant experience for the patients and medical professionals, and a higher rate of return for the physician and practice.

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. An appointment monitoring system, comprising:
a first beacon corresponding to an individual, wherein the first beacon is configured to transmit a wireless signal;
a first sensor located within a medical room, wherein the first sensor is reactive to the wireless signal or to a position or motion of the first beacon that is in a proximity to the first sensor, wherein the first sensor transmits a pulse signal with a first duration when the first beacon is in the proximity to indicate a presence of the individual in the medical room, wherein the first sensor transmits the pulse signal with a second duration when the first beacon leaves the proximity to indicate an exit of the individual from the medical room;
an appointment database comprising scheduling information including a first scheduled time for a first appointment, a second scheduled time for a second appointment;
a delay log accessible through an office interface;
a computing device programmed to display the office interface; and
a processor coupled to the first sensor, wherein the processor comprises logic capable of:

receiving an examination start time for the first appointment corresponding to when the first sensor transmits the pulse signal with the first duration,
subtracting the first scheduled time from the examination start time to compute a first delay, and
transmitting the first delay to the delay log.

2. The system of claim 1, further comprising a patient notification interface communicatively coupled to the appointment database and at least one patient device.

3. The system of claim 2, wherein the patient device comprises a telephone and the patient notification interface alerts a patient to the first delay by a text message or a voicemail.

4. The system of claim 2, wherein the patient device comprises a computing device and the patient notification interface alerts a patient to the first delay by an email or a push notification.

5. The system of claim 2, wherein the appointment database further comprises a date and time of an open appointment slot, and wherein the patient notification interface sends details of the open appointment slot to the patient device.

6. The system of claim 5, wherein the patient notification interface accepts a rescheduling message from the patient device indicating a selection of the open appointment slot and responsively updates at least one of the second scheduled time or the appointment database.

7. The system of claim 2, wherein the patient notification interface causes the patient device to display an option of keeping or rescheduling a delayed appointment.

8. The system of claim 1, wherein the first sensor activates an alert in response to the first beacon passing through a doorway.

9. The system of claim 1, wherein the individual corresponding to the first beacon is a first medical worker or a first patient corresponding to the first appointment, and wherein the first beacon is carried or worn by the first medical worker or the first patient.

10. The system of claim 1, wherein the processor further comprises logic capable of:
determining that the first delay is greater than a delay threshold; and
overwriting the second scheduled time if the first delay is greater than the delay threshold.

11. A non-transitory machine-readable storage medium programmed with code that, when executed, causes at least one machine to perform actions comprising:
detecting, via a first sensor located within a medical room, a position or a motion of a first beacon in proximity to the first sensor, the first beacon corresponding to an individual, wherein the first sensor transmits a pulse signal with a first duration when the first beacon is in the proximity to indicate a presence of the individual in the medical room, wherein the first sensor transmits the pulse signal with a second duration when the first beacon leaves the proximity to indicate an exit of the individual from the medical room;
retrieving scheduling information from an appointment database, the scheduling information including a plurality of appointments and corresponding scheduled times and duration for each appointment, wherein the scheduling information includes a first scheduled time for a first appointment and a second scheduled time for a second appointment; and
via a processor coupled to the first sensor, logging an examination start time corresponding to when the first sensor transmits the pulse signal with the first duration, subtracting the first scheduled time from the examination start time to compute a first delay, and determining that the first delay is greater than a delay threshold, adding the first delay to the second scheduled time to compute a revised time associated with the second appointment; and transmitting a notification to a communication device associated with a second patient corresponding to the second appointment, the notification including the revised time.

12. The non-transitory machine-readable storage medium of claim 11, wherein the actions further comprise:

displaying a selectable "keep" option and a selectable list of open appointments on the communication device after transmitting the notification;

in response to a selection of the selectable "keep" option, replacing the second scheduled time with the revised time; and in response to a selection of a substitute appointment from the selectable list of open appointments, canceling the second appointment and assigning the substitute appointment to the second patient.

13. The non-transitory machine-readable storage medium of claim 11, wherein the communication device comprises a remote device used by the second patient.

14. The non-transitory machine-readable storage medium of claim 11, wherein the communication device comprises a mobile device.

15. The non-transitory machine-readable storage medium of claim 11, wherein the communication device comprises a computing device used by an office staff.

16. The non-transitory machine-readable storage medium of claim 11, wherein the actions further comprise:

transmitting the first delay to a delay log accessible through an office interface, wherein the office interface is displayed via a computing device.

17. The non-transitory machine-readable storage medium of claim 11, wherein the individual corresponding to the first beacon is a first medical worker or a first patient corresponding to the first appointment, and wherein the first beacon is carried or worn by the first medical worker or the first patient.

18. The non-transitory machine-readable storage medium of claim 11, wherein the notification is transmitted as a push notification via a patient notification interface.

19. The non-transitory machine-readable storage medium of claim 11, wherein the actions further comprise:

programming the first beacon to transmit an identity signal associated with the individual; and logging an identity corresponding to the identity signal along with the examination start time.

20. The non-transitory machine-readable storage medium of claim 11, wherein the actions further comprise:

storing a log entry corresponding to the first delay in a database; and analyzing the database to identify frequent causes, lengths, or types of appointment delays.

* * * * *